US008865473B2

(12) United States Patent
Gambini et al.

(10) Patent No.: US 8,865,473 B2
(45) Date of Patent: *Oct. 21, 2014

(54) LUMINESCENCE DETECTING APPARATUSES AND METHODS

(75) Inventors: Michael Gambini, Bolton, MA (US); Jeff Levi, Trumbull, CT (US); John Voyta, Sudbury, MA (US); John Atwood, Redding, CT (US); Susan A. Atwood-Stone, legal representative, Charlotte, VT (US); Bruce E. DeSimas, II, Danville, CA (US); Edward Lakatos, Bethel, CT (US); Israel Metal, Flushing, NY (US); George Sabak, Monroe, CT (US); Yongdong Wang, Wilton, CT (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/584,628

(22) Filed: Aug. 13, 2012

(65) Prior Publication Data

US 2012/0309103 A1 Dec. 6, 2012

Related U.S. Application Data

(60) Continuation of application No. 12/716,219, filed on Mar. 2, 2010, now Pat. No. 8,278,114, which is a
(Continued)

(51) Int. Cl.
| | |
|---|---|
| *G01N 21/76* | (2006.01) |
| *G01T 1/10* | (2006.01) |
| *G01N 21/64* | (2006.01) |
| *G01N 21/27* | (2006.01) |
| *G01N 21/31* | (2006.01) |
| *G01N 21/15* | (2006.01) |

(52) U.S. Cl.
CPC ........ *G01N 21/6452* (2013.01); *G01N 21/6486* (2013.01); *G01N 2021/6471* (2013.01);
(Continued)

(58) Field of Classification Search
USPC ....... 250/332, 361 C, 361 R, 362, 363.1, 368, 250/486.1, 559.08; 356/222, 435; 422/52, 422/63–65, 67, 73, 82.08–82.09; 435/287.2–287.3, 288.4; 436/43, 47, 436/50, 172; 702/19, 25
See application file for complete search history.

(56) References Cited

U.S. PATENT DOCUMENTS 3,264,474 A * 8/1966 Heiss ............................ 250/429
3,581,308 A * 5/1971 McNaney ................ 340/815.42
(Continued)

FOREIGN PATENT DOCUMENTS

CA 2157755 * 3/1997
DE 197 482 11 5/1999
(Continued)

OTHER PUBLICATIONS

Aldridge,, P. K. et al., "Laptop Chemistry: A compact, portable thin layer scanner", *Journal of luid Chromatography*, vol. 13, 1990, 2829-2839.
(Continued)

*Primary Examiner* — Arlen Soderquist

(57) ABSTRACT

A luminescence detecting apparatus and method for analyzing luminescent samples is disclosed. A detecting apparatus may be configured so that light from luminescent samples pass through a collimator, a first lens, a filter, and a camera lens, whereupon an image is created by the optics on the charge-coupled device (CCD) camera. The detecting apparatus may further include central processing control of all operations, multiple wavelength filter wheel, and/or a robot for handling of samples and reagents.

32 Claims, 15 Drawing Sheets

Related U.S. Application Data division of application No. 11/251,873, filed on Oct. 18, 2005, now Pat. No. 7,670,848, which is a division of application No. 10/323,669, filed on Dec. 20, 2002, now abandoned, which is a continuation of application No. 09/621,961, filed on Jul. 21, 2000, now Pat. No. 6,518,068.

(60) Provisional application No. 60/144,891, filed on Jul. 21, 1999.

(52) U.S. Cl.
CPC ............. *G01N 21/274* (2013.01); *G01N 21/31* (2013.01); *G01N 21/76* (2013.01); *G01N 21/276* (2013.01); *G01N 21/15* (2013.01); *G01N 21/6456* (2013.01)
USPC ................. 436/172; 250/361 C; 250/361 R; 250/363.1; 250/368; 356/222; 356/435; 422/52; 422/65; 422/67; 422/82.08; 436/50; 702/19; 702/29

(56) References Cited

U.S. PATENT DOCUMENTS

| | | | | |
|---|---|---|---|---|
| 3,628,028 | A * | 12/1971 | Thorsheim | 250/576 |
| 3,668,395 | A * | 6/1972 | Walker | 250/363.01 |
| 3,678,564 | A * | 7/1972 | Roberts et al. | 29/419.1 |
| 3,723,746 | A * | 3/1973 | Lawson et al. | 250/574 |
| 3,745,359 | A * | 7/1973 | Martone | 250/369 |
| 3,754,866 | A * | 8/1973 | Ritchie et al. | 422/73 |
| 4,003,151 | A * | 1/1977 | Tolosa et al. | 40/575 |
| 4,004,150 | A * | 1/1977 | Natelson | 250/328 |
| 4,056,724 | A * | 11/1977 | Harte | 250/328 |
| 4,099,920 | A * | 7/1978 | Heiss | 422/52 |
| 4,126,783 | A * | 11/1978 | Lanza et al. | 250/336.2 |
| 4,190,368 | A * | 2/1980 | Etess | 356/417 |
| 4,221,867 | A * | 9/1980 | McFadden | 435/32 |
| 4,307,294 | A * | 12/1981 | Campbell | 250/201.7 |
| 4,320,841 | A * | 3/1982 | Gordon et al. | 209/552 |
| 4,366,118 | A * | 12/1982 | Bunce et al. | 422/404 |
| 4,392,746 | A * | 7/1983 | Rook et al. | 356/409 |
| 4,437,160 | A * | 3/1984 | Blum | 250/369 |
| 4,498,782 | A * | 2/1985 | Proctor et al. | 356/436 |
| 4,521,689 | A * | 6/1985 | Pritzkow | 250/385.1 |
| 4,580,895 | A * | 4/1986 | Patel | 356/39 |
| 4,597,096 | A * | 6/1986 | Larsson | 378/149 |
| 4,695,729 | A * | 9/1987 | Monno et al. | 250/358.1 |
| 4,710,031 | A * | 12/1987 | Kelly et al. | 356/440 |
| 4,762,420 | A * | 8/1988 | Bowley | 356/436 |
| 4,772,453 | A * | 9/1988 | Lisenbee | 422/52 |
| 4,810,348 | A * | 3/1989 | Sarrine et al. | 204/608 |
| 4,885,759 | A * | 12/1989 | Tomoda et al. | 378/53 |
| 4,949,079 | A * | 8/1990 | Loebner | 345/180 |
| 4,967,084 | A * | 10/1990 | Rich et al. | 250/361 R |
| 4,968,148 | A * | 11/1990 | Chow et al. | 356/427 |
| 4,986,891 | A * | 1/1991 | Sarrine et al. | 204/608 |
| 5,073,029 | A * | 12/1991 | Eberly et al. | 356/432 |
| 5,082,628 | A * | 1/1992 | Andreotti et al. | 422/82.08 |
| 5,096,835 | A * | 3/1992 | Yokomori et al. | 436/165 |
| 5,104,621 | A * | 4/1992 | Pfost et al. | 422/67 |
| 5,112,134 | A * | 5/1992 | Chow et al. | 356/427 |
| 5,144,136 | A * | 9/1992 | Kubisiak | 250/328 |
| 5,147,522 | A * | 9/1992 | Sarrine | 204/616 |
| 5,202,091 | A * | 4/1993 | Lisenbee | 422/52 |
| 5,234,665 | A * | 8/1993 | Ohta et al. | 422/73 |
| 5,268,952 | A * | 12/1993 | Tarvainen | 378/59 |
| 5,290,513 | A * | 3/1994 | Berthold et al. | 422/52 |
| 5,307,144 | A | 4/1994 | Hiroshi et al. | |
| 5,315,375 | A * | 5/1994 | Allen | 356/417 |
| 5,329,353 | A * | 7/1994 | Ichimura et al. | 356/328 |
| 5,329,461 | A * | 7/1994 | Allen et al. | 702/26 |
| 5,347,130 | A * | 9/1994 | Berthold | 250/385.1 |
| 5,355,215 | A * | 10/1994 | Schroeder et al. | 356/317 |
| 5,401,465 | A * | 3/1995 | Smethers et al. | 422/52 |
| 5,436,718 | A * | 7/1995 | Fernandes et al. | 356/73 |
| 5,567,294 | A * | 10/1996 | Dovichi et al. | 204/603 |
| 5,611,994 | A * | 3/1997 | Bailey et al. | 422/52 |
| 5,656,493 | A | 8/1997 | Mullis et al. | |
| 5,657,118 | A * | 8/1997 | Lee | 356/246 |
| 5,674,698 | A | 10/1997 | Zarling et al. | |
| 5,682,232 | A * | 10/1997 | Tajima et al. | 356/246 |
| 5,751,444 | A * | 5/1998 | Ward | 358/471 |
| 5,766,875 | A * | 6/1998 | Hafeman et al. | 435/29 |
| 5,774,214 | A * | 6/1998 | Prettyjohns | 356/344 |
| 5,784,152 | A * | 7/1998 | Heffelfinger et al. | 356/73 |
| 5,798,263 | A * | 8/1998 | Wood et al. | 435/288.7 |
| 5,854,684 | A * | 12/1998 | Stabile et al. | 356/440 |
| 5,939,024 | A * | 8/1999 | Robertson | 422/534 |
| 5,946,431 | A * | 8/1999 | Fernandes | 385/25 |
| 5,961,926 | A * | 10/1999 | Kolb et al. | 422/534 |
| 5,985,214 | A * | 11/1999 | Stylli et al. | 422/65 |
| 6,043,506 | A * | 3/2000 | Heffelfinger et al. | 250/584 |
| 6,057,163 | A * | 5/2000 | McMillan | 436/172 |
| 6,071,748 | A * | 6/2000 | Modlin et al. | 436/174 |
| 6,191,852 | B1 * | 2/2001 | Paffhausen et al. | 356/244 |
| 6,198,577 | B1 * | 3/2001 | Kedar et al. | 359/663 |
| 6,238,944 | B1 * | 5/2001 | Floyd | 438/45 |
| 6,246,525 | B1 * | 6/2001 | Ikami | 359/619 |
| 6,301,005 | B1 * | 10/2001 | Epstein et al. | 356/124 |
| 6,345,115 | B1 * | 2/2002 | Ramm et al. | 382/133 |
| 6,441,973 | B1 * | 8/2002 | Ramm et al. | 359/778 |
| 6,473,239 | B1 * | 10/2002 | Volcker et al. | 359/624 |
| 6,518,068 | B1 * | 2/2003 | Gambini et al. | 436/50 |
| 6,602,657 | B1 | 8/2003 | Bronstein | |
| 6,686,582 | B1 * | 2/2004 | Volcker et al. | 250/216 |
| 7,289,217 | B2 * | 10/2007 | Boege et al. | 356/417 |
| 7,295,316 | B2 * | 11/2007 | Boege et al. | 356/417 |
| 7,387,891 | B2 | 6/2008 | Boege et al. | |
| 7,435,602 | B2 * | 10/2008 | Gunstream et al. | 436/172 |
| 7,670,848 | B2 * | 3/2010 | Gambini et al. | 436/172 |
| 8,278,114 | B2 * | 10/2012 | Gambini et al. | 436/172 |
| 2010/0248387 | A1 | 9/2010 | Gambini et al. | |

FOREIGN PATENT DOCUMENTS

| | | | |
|---|---|---|---|
| EP | 25350 | * | 3/1981 |
| EP | 640828 | * | 3/1995 |
| EP | 753734 | * | 1/1997 |
| JP | 61-122601 | | 6/1986 |
| JP | 2239844 | | 9/1990 |
| JP | 5157684 | | 6/1993 |
| JP | 1090186 | | 4/1998 |
| JP | 10-170444 | * | 6/1998 |
| JP | 10-197449 | * | 7/1998 |
| WO | 90/02326 | * | 3/1990 |
| WO | 94/11841 | * | 5/1994 |
| WO | WO-98/26277 | | 6/1998 |
| WO | WO 99/02347 | | 5/1999 |
| WO | WO 99/60381 | | 11/1999 |
| WO | WO 00/02241 | | 4/2000 |
| WO | WO0107896 | | 2/2001 |

OTHER PUBLICATIONS

Duller, G. A. et al., "A Luminescent Imaging System based on a CCD Camera", *Radiation Measurements*, vol. 27, 1997, 91-99.

Feofanov, A et al., "A new confocal stigmatic spectrometer for micro-Raman and microfluorescence sprectral imaging analysis: Design and applications", *Review of Scientific Instruments,*, 1995, 66, 3146-3158.

Fowler,, A. et al., "A Multi-Modality Assay Platform for Ultra-High Throughput Screening", *Current Pharmaceutical Biotechnology,*, vol. 1, 2000, 265-281.

Groebe,, D. R. et al., "Use of Fluorometric Imaging Plate Reader in High-Throughput Screening", *SPIE*, vol. 3603, 1999, 297-306.

Hooper, C. E. et al., "CCD Imaging of Luciferase Gene Expression in Single Mammalian Cells", *Journal of Bioluminescence and Chemiluminescence*, vol. 5, 1990, 123-130.

Hooper, C. E. et al., "Low-Light Imaging Technology in the Life Sciences", *Journal of Bioluminescence and Chemiluminscence*, vol. 9, 1994, 113-122.

(56) References Cited

OTHER PUBLICATIONS

Jansen, E. H. et al., "A sensitive CCD Image System for Detection of Chemiluminescent Reactions", *Journal of Bioluminescence and Chemiluminscence*, vol. 3, 1989, 53-57.

Karger, Achim et al., "Imaging of fluorescent and chemiluminescent DNA hybrids using a 2-D CCD camera", *SPIE*, vol. 1206, 1990, 78-89.

Leaback, D. H. et al., "The Use of a CCD Imaging Luminometer in the Quantitation of Luminogenic Immunoassays", *Journal of Bioluminescence and Chemiluminscence*, vol. 4, 1989, 512-522.

Maly, F. E. et al., "A Single-Proton Imaging System for the Simultaneous Quantitation of Luminescent Emissions from Multiple Samples", *Analytical Biochemistry 168*, 1988, 462-469.

Maly,, F. E. et al., "A dual microtiter plate (192 sample) luminometer employing computer-aided single-photon imaging applicable to cellular luminescence and luminescence immunoassay", *Journal of Immunological Methods*, vol. 122, 1989, 91-96.

Martin,, Chris S. et al., "Imaging of Chemiluminescent Signals with Cooled CCD Camera Systems", *Journal of Bioluminescence and Chemiluminescence*, vol. 9, 1994, 145-153.

Nicholas, J. C. et al., "Applications of Low-Light Imaging to Life Sciences", *Journal of Bioluminescence and Chemiluminescence*, vol. 9, 1994, 139-144.

Oldenburg, K R. et al., *Journal of Biomolecular Screening*, 3, 1998, 55-62.

Porakishvili, Nino et al., "A low budge luminometer for sensitive chemiluminescent immunoassays", *Journal of Immunological Methods*, vol. 1, 2000, 265-281.

Roda,, A. et al., *Analytical Biochemistry*, vol. 257, 1998, 53-62.

Sadler,, Daran A. et al., "Automatic Wavelength Calibration Procedure for Use with an Optical Spectrometer and Array Detector", *Journal of Analytical Atomic Spectometry*, vol. 10, 1995, 253-257.

\* cited by examiner

LUMINESCENCE DETECTING APPARATUSES AND METHODS

RELATED APPLICATIONS

This application is a continuation of U.S. application Ser. No. 12/716,219, filed Mar. 2, 2010, now U.S. Pat. No. 8,278,114, which is a divisional of U.S. application Ser. No. 11/251,873, filed Oct. 18, 2005, now U.S. Pat. No. 7,670,848, which is a divisional of U.S. application Ser. No. 10/323,669, filed Dec. 20, 2002, now abandoned, which is a continuation of U.S. application Ser. No. 09/621,961, filed Jul. 21, 2000, now U.S. Pat. No. 6,518,068, which claims priority to U.S. provisional application No. 60/144,891, filed Jul. 21, 1999, the entire contents of each of which applications are hereby incorporated by reference in their entirety for all purposes as if fully set forth herein.

FIELD OF THE INVENTION

This invention relates to the field of apparatus and methods for detecting and quantifying light emissions, and more particularly, to detecting and quantifying light emitted from luminescent-based assays. Still more particularly, this invention pertains to apparatus and methods for detecting and quantifying luminescence such as bioluminescence and/or chemiluminescence from luminescent assays as an indicator of the presence or amount of a target compound. Preferred embodiments of the invention include as an imaging device a charge coupled device (CCD) camera and a computer for analyzing data collected by the imaging device. Further preferred embodiments include the capacity for use in high throughput screening (HTS) applications, and provide for robot handling of assay plates.

DESCRIPTION OF THE RELATED ART

The analysis of the luminescence of a substance, and specifically the analysis of either bioluminescence (BL) or chemiluminescence (CL), is becoming an increasingly useful method of making quantitative determinations of a variety of luminescent analytes.

Recently, methods have been introduced that utilize luminescence detection for quantitatively analyzing analytes in an immunoassay protocol. Such luminescence immunoassays (LIA) offer the potential of combining the reaction specificity of immunospecific antibodies or hybridizing nucleic acid sequences and similar specific ligands with the high sensitivity available through light detection. Traditionally, radioactive reagents have been used for such purposes, and the specificity and sensitivity of LIA reagents is generally comparable to those employing traditional radiolabelling. However, LIA is the preferred analytical method for many applications, owing to the nontoxic nature of LIA reagents and the longer shelf lives of LIA reagents relative to radioactive reagents.

Among other luminescent reagents, chemiluminescent compounds such as 1,2-dioxetanes, developed by Tropix, Inc. and other stable chemiluminescent molecules, such as xanthan esters and the like, are in commercial use. These compounds are triggered to release light through decomposition triggered by an agent, frequently an enzyme such as alkaline phosphatase, which is present only in the presence, or specific absence, of the target compound. The detection of light emission is a qualitative indication, and the amount of light emitted can be quantified as an indicator of the amount of triggering agent, and therefore target compound, present. Other well known luminescent compounds can be used as well.

Luminescent release may sometimes be enhanced by the presence of an enhancement agent that amplifies or increases the amount of light released. This can be achieved by using agents which sequester the luminescent reagents in a microenvironment which reduces suppression of light emission. Much biological work is done, perforce, in aqueous media. Water typically suppresses light emission. By providing compounds, such as water soluble polymeric onium salts (ammonium, phosphonium, sulfonium, etc.) small regions where water is excluded that may sequester the light emitting compound may be provided.

The majority of instrumentation used to monitor light emitting reactions (luminometers) use one or more photomultiplier tubes (PMTs) to detect the photons emitted. These are designed to detect light at the low light levels associated with luminescent reactions. The rate at which a PMT based microplate luminometer can measure signal from all wells of the plate is limited by the number of PMTs used. Most microplate luminometers have only one PMT so a 384 well plate requires four times longer than is required to read a 96-well plate.

The nature of biological research dictates that numerous samples be assayed concurrently, e.g., for reaction of a chemiluminescent substrate with an enzyme. This is particularly true in gene screening and drug discovery, where thousands of samples varying by concentration, composition, media, etc. must be tested. This requires that multiple samples be reacted simultaneously, and screened for luminescence. However, there is a need for high speed processing, as the chemiluminescence or bioluminescence may diminish with time. Simultaneously screening multiple samples results in improved data collection times, which subsequently permits faster data analysis, and contingent improved reliability of the analyzed data.

In order for each specific sample analyte's luminescence to be analyzed with the desired degree of accuracy, the light emission from each sample must be isolated from the samples being analyzed concurrently. In such circumstances, stray light from external light sources or adjacent samples, even when those light levels are low, can be problematic. Conventional assays, particularly those employing high throughput screening (HTS) use microplates, plastic trays provided with multiple wells, as separate reaction chambers to accommodate the many samples to be tested. Plates currently in use include 96- and 384-well plates. In response to the increasing demand for HTS speed and miniaturization, plates having 1,536 wells are being introduced. An especially difficult impediment to accurate luminescence analysis is the inadvertent detection of light in sample wells adjacent to wells with high signal intensity. This phenomenon of light measurement interference by adjacent samples is termed 'crosstalk' and can lead to assignment of erroneous values to samples in the adjacent wells if the signal in those wells is actually weak.

Some previously proposed luminometers include those described in U.S. Pat. No. 4,772,453; U.S. Pat. No. 4,366,118; and European Patent No. EP 0025350. U.S. Pat. No. 4,772,453 describes a luminometer having a fixed photodetector positioned above a platform carrying a plurality of sample cells. Each cell is positioned in turn under an aperture through which light from the sample is directed to the photodetector. U.S. Pat. No. 4,366,118 describes a luminometer in which light emitted from a linear array of samples is detected laterally instead of above the sample. Finally, EP 0025350 describes a luminometer in which light emitted through the bottom of a sample well is detected by a movable photodetector array positioned underneath the wells.

Further refinements of luminometers have been proposed in which a liquid injection system for initiating the luminescence reaction just prior to detection is employed, as disclosed in EP 0025350. Also, a temperature control mechanism has been proposed for use in a luminometer in U.S. Pat. No. 4,099,920. Control of the temperature of luminescent samples may be important, for example, when it is desired to incubate the samples at an elevated temperature.

A variety of light detection systems for HTS applications are available in the market. These include the LEADseeker™ from Amersham/Pharmacia, the ViewLux™ offered by PerkinElmer and CLIPR™ from Molecular Devices. These devices are all expensive, large dimensioned (floorbased models), exhibit only limited compatibility with robotic devices for plate preparation and loading, have a limited dynamic range, and/or use optical detection methods which do not reduce, or account for, crosstalk. The optical systems used are typically complex teleconcentric glass lens systems, which may provide a distorted view of wells at the edges of the plates, and the systems are frequently expensive, costing in excess of $200,000.00. Perhaps the most popular detection apparatus is the TopCount™, a PMT-based detection system from Packard. Although the TopCount™ device has a desirable dynamic range, it is not capable of reading 1,536 well plates, and it does not image the whole plate simultaneously.

Crosstalk from adjacent samples remains a significant obstacle to the development of improved luminescence analysis in imaging-based systems. This can be appreciated as a phenomenon of simple optics, where luminescent samples produce stray light which can interfere with the light from adjacent samples. Furthermore, the development of luminometers capable of detecting and analyzing samples with extremely low light levels are particularly vulnerable to crosstalk interference.

SUMMARY OF THE INVENTION

In order to meet the above-identified needs that are unsatisfied by the prior art, it is a principal object and purpose of the present invention to provide a luminescence detecting apparatus that will permit the analysis of luminescent samples. It is a further object of the present invention to provide a luminescence detecting apparatus capable of simultaneously analyzing a large number of luminescent samples. In a preferred embodiment of the present invention, a luminescence detecting apparatus is provided that simultaneously analyzes multiple samples held in wells, where the well plates contain as many as 1,536 wells. The present invention further includes robot handling of the multiple well trays during analysis.

It is yet another object of the present invention to provide a luminescence detecting apparatus capable of analyzing low light level luminescent samples, while minimizing crosstalk from adjacent samples, including and especially minimizing crosstalk from adjacent samples with higher light level output than the sample to be analyzed.

The apparatus of this invention employs a Fresnel lens arrangement, with a vertical collimator above the well plate, with dimensions to match the number of wells. Thus, a 1,536-well plate will employ a dark collimator above the plate with 1,536 cells in registry with the wells of the plate. Fixed above the collimator is a Fresnel lens, which refracts the light such that the view above the lens appears to be looking straight down into each well, regardless of its position on the plate, even at the edges.

Above the Fresnel lens is a CCD camera arranged so as to take the image of the entire plate at one time, viewing through a 35 mm wide angle lens, to give whole plate imaging on a rapid basis. Between the CCD and Fresnel/collimator is a filter, typically arrayed on a filter wheel, disposed at an angle to the lens. The filter is selected to permit the passage of the specific wavelength of the light emitted, and reflect or absorb all others. Several filters may be provided on the wheel, to permit sequential detection of light emitted from multiple reagents emitting light at different wavelengths.

The samples are fed to the optical detection platform through a loading device designed to work well with robotic and automated preparation systems. The well-plate, with reaction mixture already provided, is placed on a shuttle by a human, or preferably, robot. Alignment of the plate on the shuttle may be relatively coarse, notwithstanding the requirement for tight tolerances to match the collimator grid array. As the shuttle leaves the loading position, a resilient means urges the plate into strict conformal alignment. The shuttle positions the plate under an overhead injection bar, which may accommodate up to sixteen wells in a column at one time. If not previously added, a triggering agent or luminescent reagent is added to the sample wells, and the plate indexes forward to load the next column of wells across the plate. The shuttle then advances through a door into the sample chamber, and the plate is aligned with the collimator and the Fresnel lens. Since many reactions proceed better, or only, at elevated temperatures, the sample chamber is insulated, and provided with heating means, for heating the air in or provided to the chamber. In order to maintain temperature in the chamber close to room temperature and to accurately control temperature, the chamber may also be provided with a heat exchanger.

The light emission from the entire multiple well plate is imaged at once, with subsequent imaging through a different filter if multiple wavelengths are employed. The signal obtained is processed to further reduce crosstalk reduced by the collimator and the presence and amount of luminescence is quickly detected and calculated by a personal computer using automated software. Data is then reported as intensity per well or further analyzed relative to specific assay standards.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
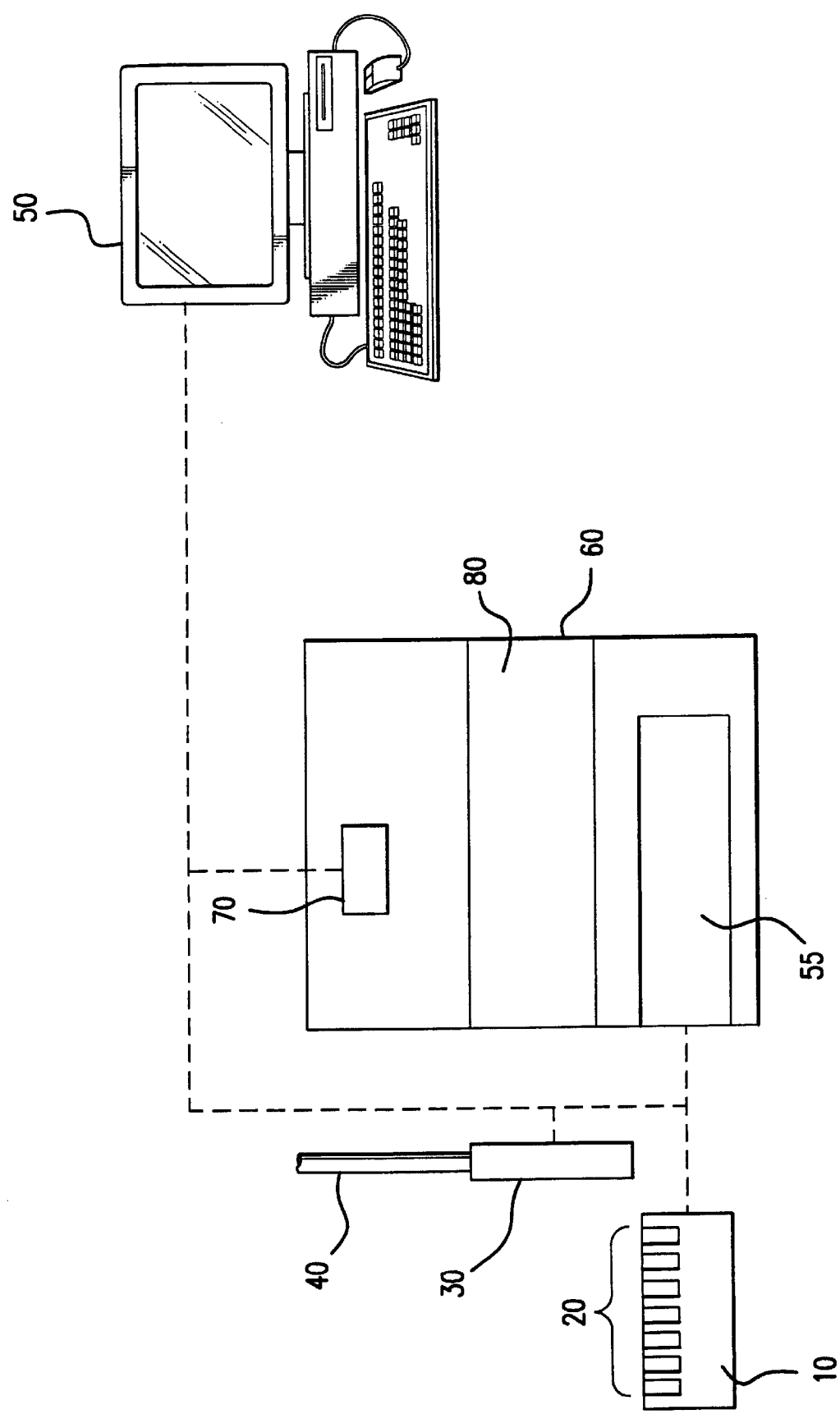
FIG. 1 is a cross section of a preferred embodiment of a luminescence detecting apparatus according to the present invention.

Referring now to the drawings, wherein like reference numerals designate identical or corresponding parts throughout the several views, and more particularly to FIG. 1 thereof, a preferred embodiment of the luminescence detecting apparatus of the present invention uses a shuttle or tray to carry a micro plate (plate) 10 comprising a plurality of sample wells 20 which may in the preferred embodiment number as many as 1,536 or more. Persons of ordinary skill in the relevant art will recognize that the number of sample wells 20 is limited only by the physical dimensions and optical characteristics of the luminometer elements, and not by the technology of the present invention. The sample wells 20 may be filled with analyte manually, or robotically prior to delivery to the inventive apparatus. Agents necessary for chemiluminescence may be filled automatically via the injector 30, to which analyte is supplied through an array of supply tubes 40 or prior to placing the plate on the tray. Typically, the sample wells will contain chemiluminescent reagents. These reagents emit light at intensities proportional to the concentration of analyte in the sample. This light can be very low intensity and requires an instrument with sufficient sensitivity to achieve the desired detection limits.

The operation of injector 30 is controlled by central processor 50, which in the preferred embodiment may control the operation of all elements of the luminometer of the present invention. Data collection, analysis and presentation may also be controlled by processor 50. Further in a preferred embodiment of the present invention, the injector 30 may also be used to add buffer solutions to the analytes and also to add reagents that enable "glow" and/or "flash" luminescence imaging, that is sustained or brief, intense emission, respectively, all under control of central processor 50.

After the analytes are placed in the sample wells 20, plate 10 is placed in sample chamber 55, which is located in optical chamber 60 at a fixed focal distance from and directly under the charge-coupled device (CCD) camera 70, in order to permit the CCD camera to image the luminescent sample accurately. The sample chamber 55 is preferably capable of precise temperature control, as many luminescent reagents and specific luminescent reactions are temperature dependent. Temperature control is provided by central processor 50, which can vary the temperature for each individual sample plate 10, as central processor 50 controls the movement and injection of the sample wells 20 in each sample tray 10. In a preferred embodiment of the luminometer of the present invention, central processor 50 also controls an industrial robot (not shown) which performs the activities involving analyte handling in the luminometer of the present invention.

With the plate 10 placed in the sample chamber 55, the optics 80 deliver the image of the complete microplate 10 as a single image to the CCD camera 70.

Although the operation of the luminometer of this invention is an integral, continuous practice, and all elements of the luminometer cooperate together to provide precise, accurate and reliable data, the invention may be more easily understood by reference to three separate, integrated systems, the optics system, the mechanical system and the processing system. Each is discussed in turn, with a discussion of examples of the operation as a whole to follow.

Optics System

Figure 2:
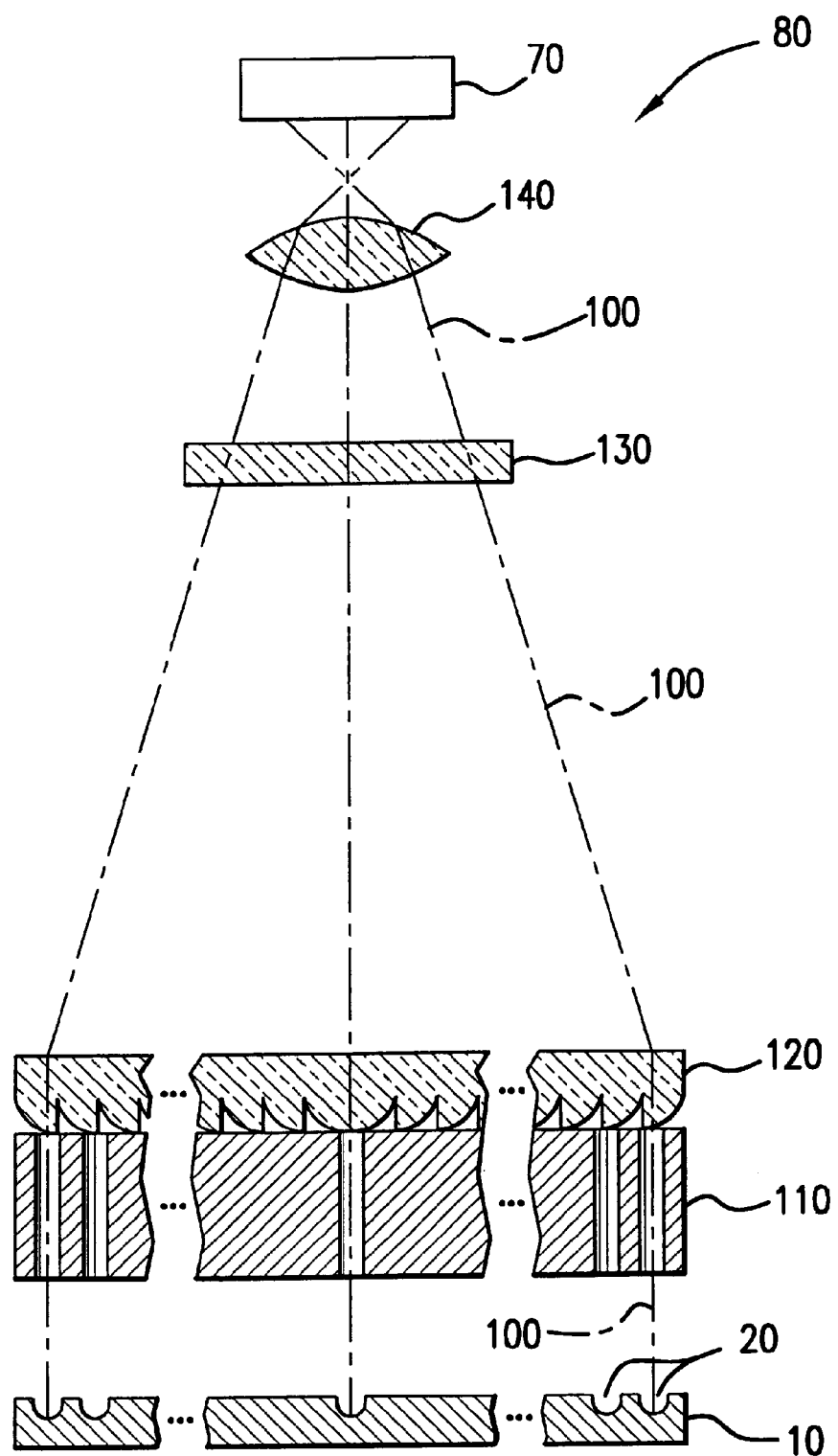
FIG. 2 is a detailed cross section of the optics of a luminescence detecting apparatus according to the present invention.

Turning now to FIG. 2, the optics 80 are shown in further detail. Luminescent emission 100 from the analyte in plate well 20 located in the plate 10 travels first through dark collimator 110, which permits only parallel and semi-parallel light rays to exit the sample wells 20 for eventual imaging by the CCD camera 70. The effect of collimation assists with the prevention of stray light from the sample wells 20 and with the elimination of crosstalk between luminescent samples. The collimator 110 may be sealably engaged, or in close proximity, to the sample tray 10, to enhance the restriction of stray light from the samples. Each well 10 is in strict registration and alignment with a corresponding grid opening in collimator 110. From the collimator 110, the luminescent radiation passes through a Fresnel field lens 120, which focuses the light toward filter 130. In a preferred embodiment of the present invention, the collimator 110 and Fresnel field lens 120 are packaged in a cassette that can be changed by the user. Such an equipment change may be necessitated by varying optical characteristics of different analytes and different well distributions in plates.

The use of a Fresnel field lens is preferable to alternative optical devices for several reasons. Initially, improvements in design and materials have capitalized on the superior optical capabilities of the Fresnel lens, while virtually eliminating its once inherent limitations. Today, many Fresnel lenses are made of molded plastic, creating an almost flawless surface with very little scatter light. The elimination of scatter light is an important element of eliminating crosstalk between adjacent samples in the luminometer of the present invention. Furthermore, improved types of plastics commonly employed in the manufacturing of Fresnel lenses and other optical devices have optical qualities equivalent to ground glass lenses.

Using high tech processes such as computer-controlled diamond turning, complex aspheric surfaces can be cut into a long lasting mold for casting Fresnel lenses. In this manner, Fresnel lenses can be manufactured to produce the precise optical imaging effect that is most efficient for a charge coupled device camera, as in the present invention. Also, Fresnel lenses offer an advantage over conventional lenses in that they can be molded flat and very thin. Because of the shape of the Fresnel lens, it can easily be integrated directly into the housing of the luminometer, enhancing the light-tight properties necessary for accurate imaging of low light samples. Furthermore, Fresnel lenses are much less expensive than comparable conventional glass lenses.

As with any other lens, the total beam spread from a Fresnel lens depends on the size of the source in relation to the focal length of the lens. Smaller sources, such as luminescent assay samples, and longer focal lengths produce more compact beams. Since there are practical limitations to minimizing the geometry and dimensions of the optics 80 in the luminometer of the present invention, the use of Fresnel field lens 120 provides the greatest opportunity for fine-tuned optics. The emissions from plate 10 pass through lens 120, and are refracted such that the image obtained at CCD 70 appears to look directly downward into all wells, even laterally displaced (edge) ones. This feature is typically called "telecentric."

Further in a preferred embodiment of the present invention, the filter 130 may be configured on a wheel, wherein different filter elements may occupy different portions of the wheel, depending on the luminescent characteristics of the sample being analyzed. Filter 130 is preferably inclined at an angle of 20°-30° relative to the CCD, so that stray reflected light is reflected outside the field of view. Specifically, the filter wheel 130 permits the selection of different wavelength ranges, which not only permit high quality imaging, but may be used to separate the emissions of different reagents emitting at different wavelengths. Again, the filter wheel 130 is controlled by central processor 50, in coordination with central processor 50's control of the individual sample wells 20 in the sample plate 10. In many assays, such as those addressed in pending U.S. patent application Ser. No. 08/579,787, incorporated by reference herein, multiple luminescent reagents, which emit at different wavelengths, are employed in a single well. Using multiple filters, each can be imaged in turn, and the true concentration can be calculated from the data set resulting using pre-stored calibration factors. Filter 130 is preferably provided with an infrared (IR) filter operating in conjunction with the selected bandpass, or as an independent element. Applicants have discovered that stray IR radiation, resulting from the plate phosphorescence, resulting in abnormally high backgrounds. An IR filter suppresses this.

From the filter wheel 130, the sample-emitted light passes through camera lens 140, which in the preferred embodiment is a large aperture, low distortion, camera lens. Camera lens 140 focuses the image of the sample on the CCD chip 70. In the preferred embodiment of the present invention, CCD camera 70 is a cooled, low noise, high resolution device. The lens is preferably a 35 mm wide angle lens with a low light level (F 1.4) large aperture character. Magnification of 3-6, preferably about 5.5, is preferred. In preferred embodiments CCD camera 70 is provided with an anti-blooming CCD chip, to enhance dynamic range, which is about $10^5$ in the claimed invention, referred to as the NorthStar™ luminometer. Blooming occurs when a single pixel is overloaded with light and its photoelectrons overflow the CCD device well capacity, obliterating surrounding pixels. Further in the preferred embodiment of the luminometer of the present invention, the selected CCD camera includes a liquid cooled thermoelectric (Peltier) device providing cooling of the CCD to approximately −35° C., and the CCD has 1280×1024 pixels, each of which are 16 μm square, producing a total active area of 20.5 mm×16.4 mm. The quantum efficiency averages 15% over the range from 450 nanometers to 800 nm. The output is digitized to 16 bit precision and pixels can be "binned" to reduce electronic noise.

By using the features disclosed herein, the luminometer of the present invention has a spatial resolution capable of providing high quality imaging of high density, sample trays. The noise performance and CCD temperature are designed to provide the desired detection limit.

Mechanics

Figure 3:
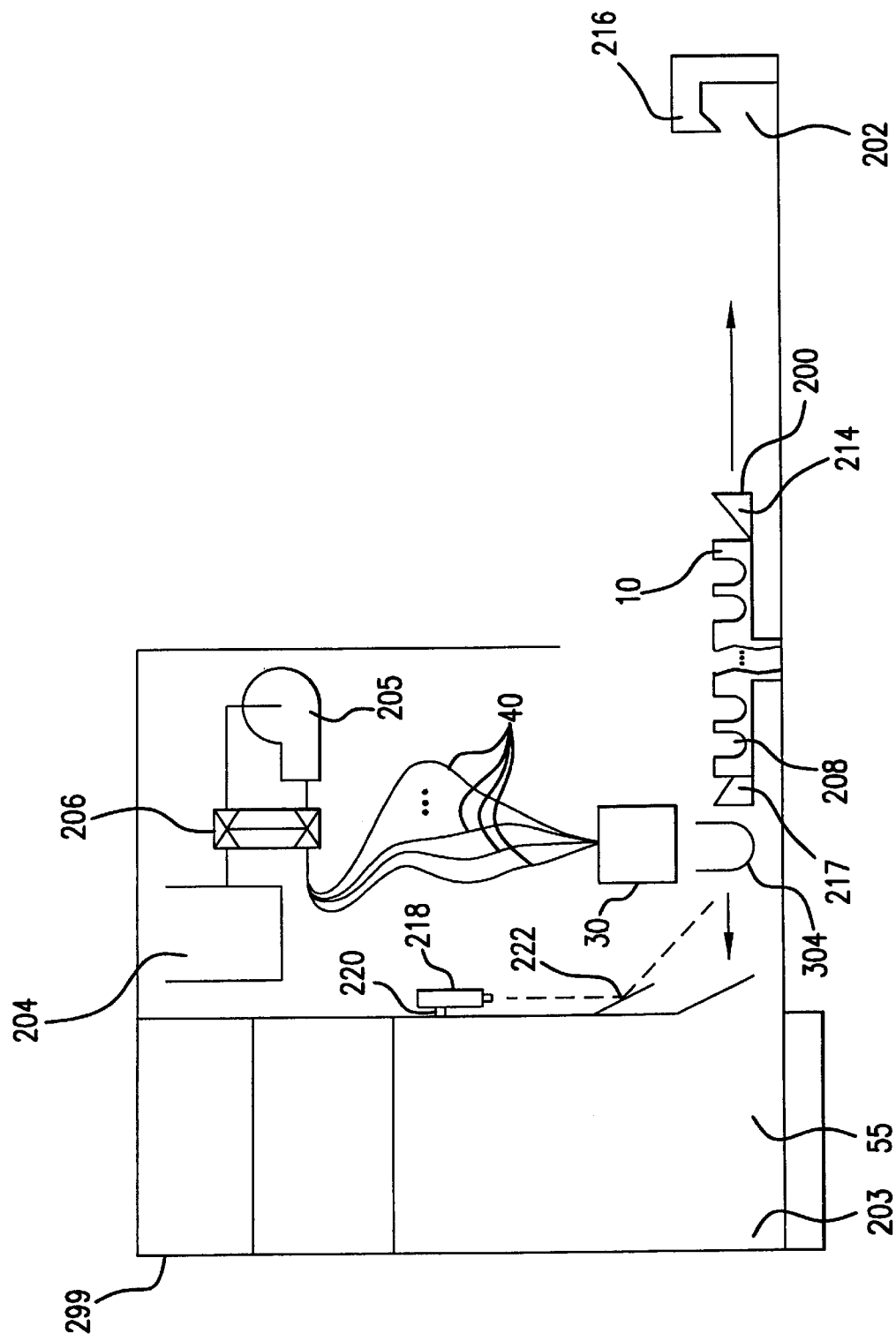
FIG. 3 is a cross-sectional view of the plate transport system of the invention.

The mechanical systems of the luminometer workstation of this invention are designed to achieve automated, high throughput precise delivery of microplates in registration with a collimator 110 so as to be read by the CCD Camera 70. To this end, as shown in FIG. 3, a cross-section of the inventive luminometer shuttle 200 translates from a load position 202, where plates 10 are loaded on to the shuttle, preferably by a robotic device such as robot arm, and the shuttle 200 then translates towards sample chamber 55, to read position 203. Shuttle 200 is caused to translate by a conventional stepper motor (not pictured). As shuttle 200 advances toward sample chamber 55, it may stop underneath injector 30. Injector 30 is more fully illustrated below in FIG. 4. Referring still to FIG. 3, injector 30 delivers fluid reagents drawn from reservoir 204. Syringe pump 205 draws the fluid reagents from reservoir 204, and pumps the fluid to the injector tubes 40. Two way valve 206 controls the passage of the fluid drawn by syringe pump 205 from reservoir 204 and pumped by syringe pump 205 to the supply tubes 40. In actual practice, there are as many injector tubes 40 as injection ports being used, and multiple syringe pumps 205 are also used. As will be shown below in FIG. 4, injector 30 has up to sixteen injection ports 302. The plates used in conjunction with the luminometer when injection is used are typically prepared with up to sixteen wells in a column. As the shuttle 200 advances plate 10 underneath injector 30, shuttle 200 stops so that the first column 208 of wells is directly aligned under injector 30. Precise amounts of analyte are delivered to the first set of wells, and shuttle 200 indexes forward one column, so as to inject reagent into the second column of wells 210. This process is repeated until all wells are filled. Thereafter, shuttle 200 advances forward into sample chamber 55 through hinged door 212. In the alternative, door 212 may be a guillotine door or similar type of closing mechanism. The wells of plate 10 are then read in sample chamber 55. Upon completion of reading, shuttle 200 translates back to load position 202.

Before shuttle 200 advances to the injection bar, it may be necessary to fully prime the tube with fluid, so as to provide for precise delivery into the plate. Trough 304 swings out from its storage position parallel to the direction of travel of shuttle 200, shown by an arrow, to a position directly underlying the injector 30, perpendicular to the direction of travel. Fluid in the injector and tubes 204 are delivered into trough 304, and removed by suction. Trough 304 then returns to its rest position, parallel to, and away from, the direction of travel of the shuttle 200, when the shuttle is moved toward the sample chamber 55. On its return trip to load position 202, locator 214 on shuttle 200 is engaged by cam 216. Locator 214 is mounted on a resilient means, such that when engaged by cam 216, the locator 214 recesses away from plate 10. This permits removal of plate 10, and delivery from a robotic arm or other source of a fresh plate 10, without the requirement of precise location. As shuttle 200 moves away from load 202, locator 214 is urged forward, firmly locating plate 10 in place. Plate 10 is held against shoulder 217 by the resilient urging of locator 214.

It is important that each plate be precisely identified, so that results are correlated with the correct test samples. In most HTS laboratories, most microplates are labeled with a unique "bar code." The label is often placed on the surface perpendicular to the plane of the plate itself. To permit precise identification of each plate, a bar code reader 218 is mounted on the luminometer housing generally indicated at 299 and directly above the door 212, for example on an arm or flange 220. Bar code reader 218 is focused on a mirror 222 which in turn permits reading directly off the front or leading edge of plate 10 as it approaches on shuttle 200. Thus, before each plate arrives in the sample chamber, its identity has been precisely recorded in processor 50, and the results obtained can be correlated therewith. Persons of ordinary skill in the art will recognize that a variety of configurations of alignment and placement of both bar code reader 218 and mirror 222 will result in the desired identification.

Figure 4:
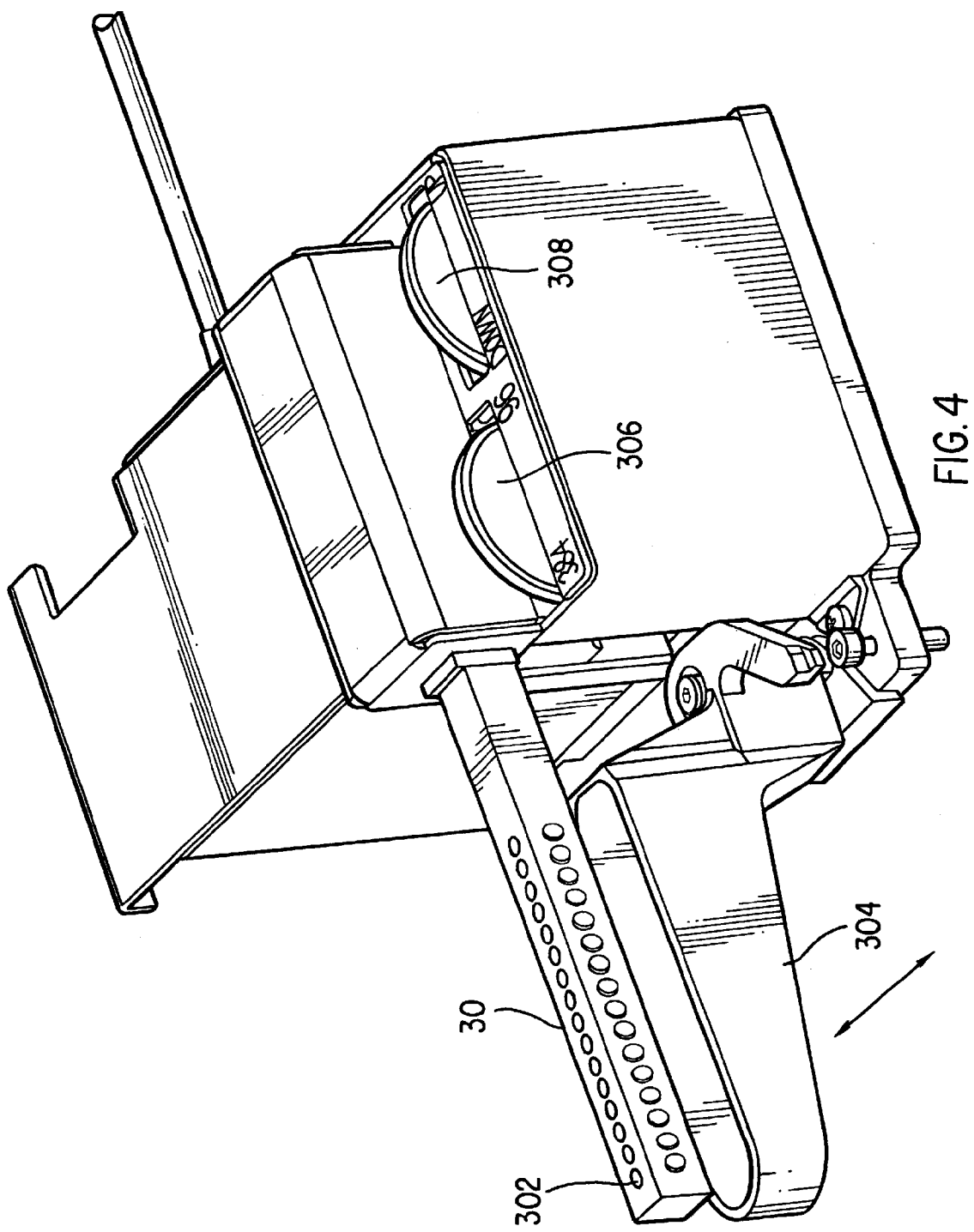
FIG. 4 is a perspective illustration of the injector arm assembly of the invention.

As more clearly shown in FIG. 4, injector 30 may be precisely located by operation of actuator wheel 306, provided with positions corresponding to the total number of wells on the plates being assayed. Similarly, the vertical position, to account for the different thicknesses of the plate, may be controlled by wheel 308. Given the simple translation movement of shuttle 200, and the precise locating and identification of each plate carried, rapid cycling of micro-plate test plates into and out of sample chamber 55 can be effected.

Figure 5:
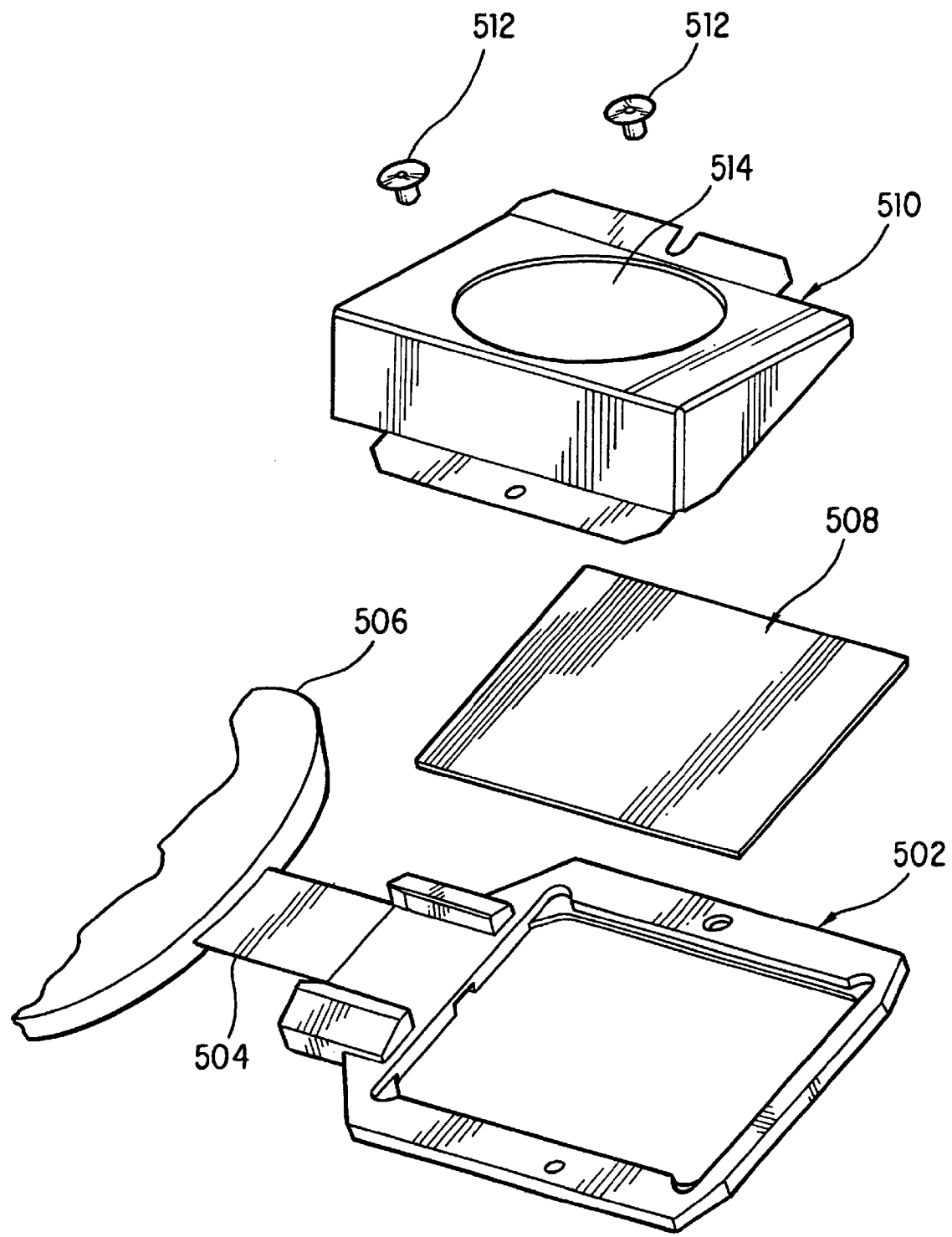
FIG. 5 is an exploded view of the filter wheel assembly.

As described above in connection with the optics system of the invention, a filter is provided which includes or reflects passage of light other than light falling within the selected wavelength of the luminescent emitter in use. The filter assembly is illustrated in exploded format in FIG. 5. Filter frame 502 is supported by arm 504 which is connected to the hub of the filter wheel 506. Multiple different filters may be provided on a single wheel. The filter itself, 508, is securely mounted on the frame and held there by cover 510, which is secured to frame 502 by grommets, screws or other holding devices 512. As noted, filter wheel is positioned so as to hold filter 508 in frame 502 at in incline with respect to collimator 110, of about 22° nominally, so as to direct any reflections outside the field of view. Light passes through the filter opening 514, in alignment with camera lens 140 and CCD camera 70. As further noted above, filter 508 preferably includes an infrared block, either as a component of the filter itself, or as a component provided in addition to the filter for the measured light. An IR block is of value to prevent infrared emissions caused by extraneous radiation from altering the image received by the CCD camera.

Figure 6:
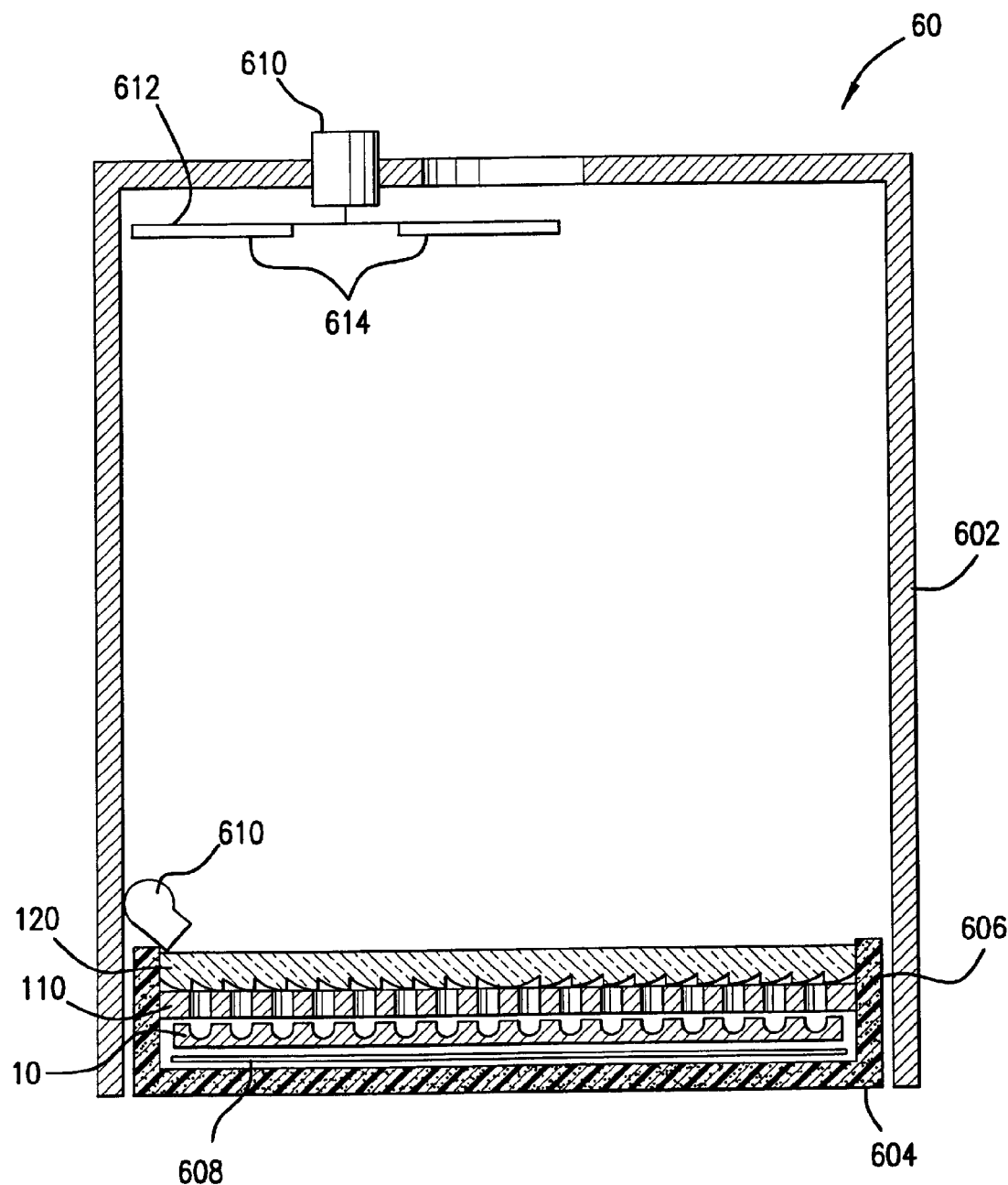
FIG. 6 is a cross-sectional view of the optical housing.

Optical chamber 60 is more fully illustrated in FIG. 6. As shown, optical chamber 60 is bounded by optical housing 602 in which fits sample housing 604. When a plate 10 is loaded into optical chamber 60, the plate is secured in sample housing 604 which is positioned in registry with collimator 110, over which is provided Fresnel lens 120. While many luminescent assays can be provided at ambient temperatures, some require elevated temperatures. The luminometer of this device is provided with a sample chamber in which the sample housing 604 carries insulation 606 which, in a preferred embodiment is polyurethane foam, and heater element 608 to raise the temperature in the sample chamber 55 above ambient temperature, up to about 42° C.

There is a tendency, even at ambient conditions, for condensation to collect on the surface of the Fresnel lens 120, as a result of moisture coming from the filled wells of plate 10. The defogger 610 directs a stream of air heated just a few degrees, preferably about 2-3° degrees, above ambient conditions, or above the temperature of the chamber if the chamber is above ambient conditions, across the surface of the Fresnel lens 120, effectively preventing condensation. Mounted at the top of the interior of optical chamber 60 is filter motor 610 which drives filter wheel 612, on which may be mounted filters 614 of varying wavelength, for filtering undesirable wavelengths prior to imaging. Of course, a region is provided, indicated at 616, in the optical housing 602 of the optical chamber 60 for light to be directed onto the CCD camera after passing through the filter 614. The dimensions of optical chamber 60 are exaggerated in FIG. 6 to illustrate the relationship between the optical chamber 60 and the filter wheel 612, and defogger 610. In practice, the filter is located inside the optical chamber 60, and outside the sample housing 604 but alternate locations are possible while still achieving the desired function.

Figure 6A:
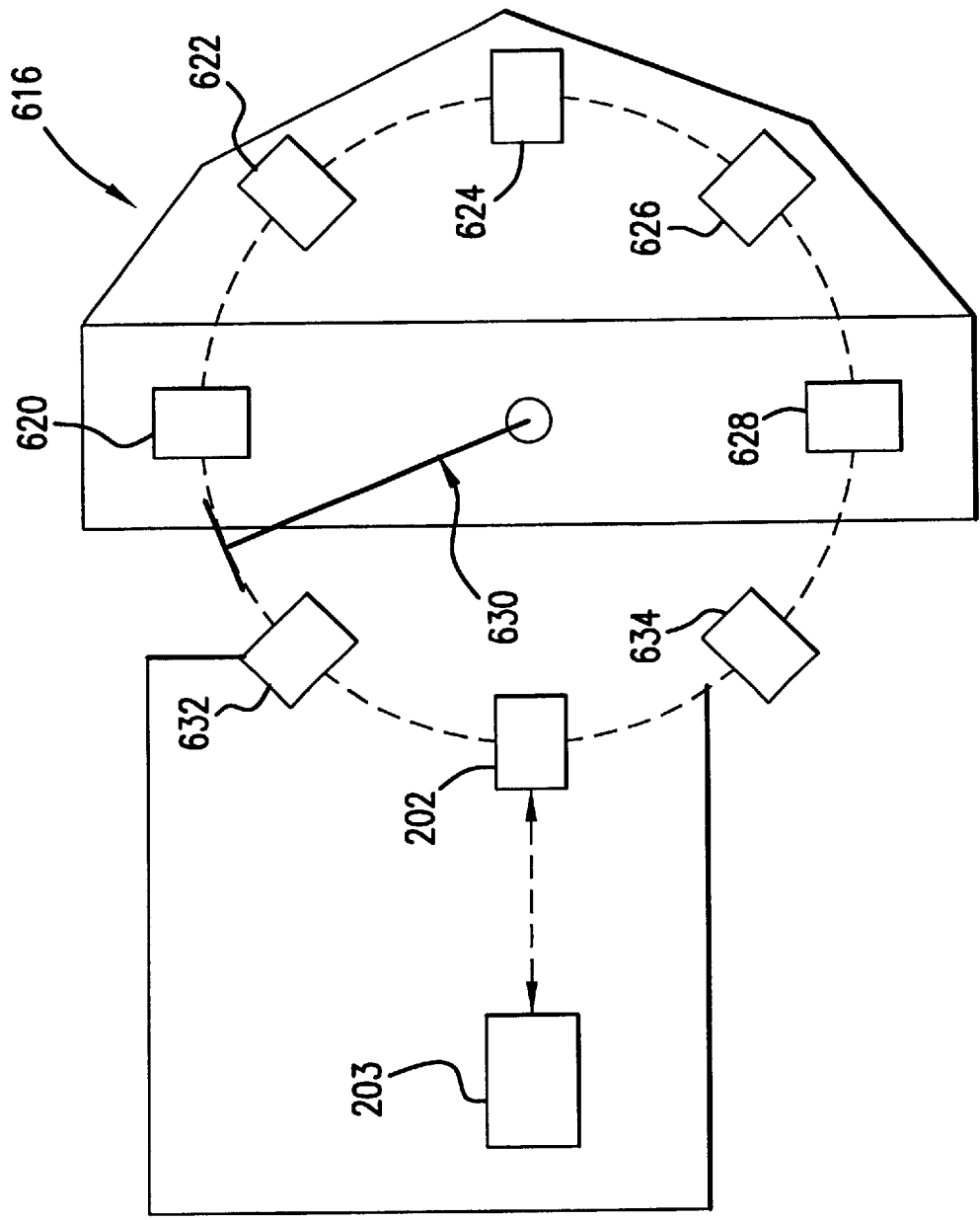
FIG. 6A is a plan view of a robotic mechanism of the invention.

In FIG. 6A, a plan view of a novel robotic mechanism 616 is displayed in a preferred embodiment of the present invention, which provides capacity for use in high throughput screening (HTS) applications. Referring to FIG. 6A, the operation is as follows: robot plate stacks 620, 622, 624, 626, and 628 each can be filled with multiple sample plates 10, arranged in a vertical stack. In the preferred embodiment of FIG. 6A, robot plate stack 628 is designated as the discard stack. The remaining robot plate stacks 620, 622, 624, and 626 can be programmed in order of delivery by software controlled by processor 50 (not shown). In order to load or pick plates from any of these stacks, robot arm 630 moves vertically and rotationally to the desired robot plate stack, under control of the software programmed in processor 50.

When commanded by processor 50, transport 200 of the instrument will move the sample plate 10 from load position 202 to the Read position 203, and return it to load position 202 when imaging is complete. In the embodiment of the invention shown in FIG. 6A, the elapsed time between moving the sample plate 10 from load position 202 to the read position 203, and returning it to load position 202 is typically 30-120 seconds, including imaging time.

Staging positions 632 and 634 are located at 45 degree positions relative to the position of robot arm 630. In one embodiment, while imaging is in process, the robot arm 630 can place a sample plate 10 at staging position 632, in preparation for placing the sample plate 10 in load position 202. When the imaging is complete, the robot can move the read plate from load position 202 to staging position 634, then load the plate from staging position 632 to load position 202, and while the sample plate 10 is being imaged, the robot can move the plate from staging position 634 to the discard stack 628, and place a new sample plate 10 at staging position 632. In practice, the staging positions are at approximately the same level as the load position, so movement is very quick. In the preferred embodiment, the robot arm 630 can do the time consuming moves to any of robot plate stacks 620, 622, 624, and 626 while imaging is going on, rather than in series with imaging.

With the staging positions 632 and 634, the cycle time for a single sample plate 10 is 2 moves from/to staging areas (3 seconds each), plus 2 transport moves IN/OUT to read position 203 (3 seconds each), plus the integration time (image exposure) time (typically 60 seconds), for a total cycle time of 72 seconds. Without using staging positions 632 and 634, the time would be 2 moves to stacks (30 seconds each), plus 2 transports (3 seconds each), plus the integration time (typically 60 seconds) for a total of 126 seconds. As described in the preferred embodiment of the robotic mechanism 616, the use of staging positions 632 and 634 decreases cycle time by 43%.

Processing

Figure 7:
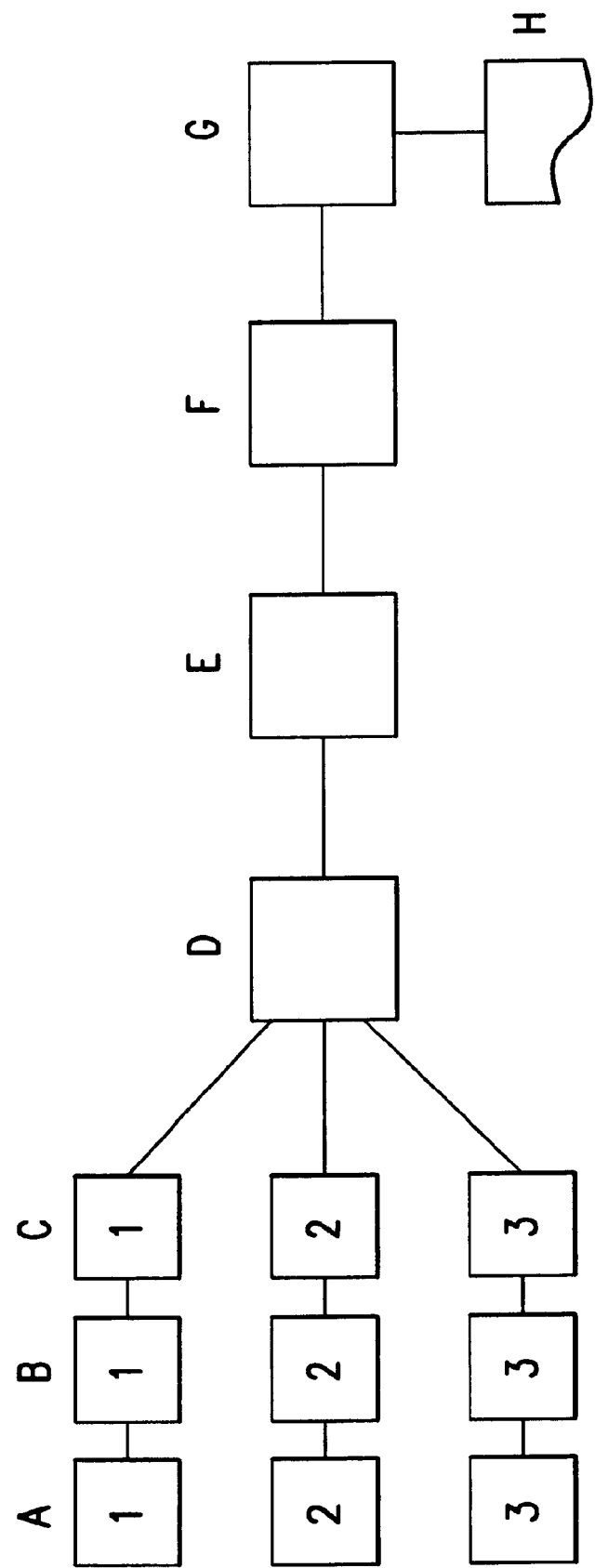
FIG. 7 is a flow chart illustration of the processing method of the invention.

As set forth above, the mechanical and optical systems of the luminometer workstation of the invention are designed to provide precise, quantified luminescent values in an HTS environment, taking advantage of the use of a Fresnel lens/collimator assembly to permit single image viewing by the CCD camera, and subsequent analysis. The collimator, the lens and the camera together combine to reduce cross-talk experienced in prior art attempts. The signals obtained are further processed, as illustrated in FIG. 7, through software loaded onto processor 50, or other convenient method, to further refine the values obtained.

Prior to processing image data collected through the integrated mechanical and optical systems of the invention herein described, the integrated processing component of the invention must first control the mechanical alignment of those integrated mechanical and optical systems for reliable data collection. This process is conducted under control of the processor 50. To conduct an alignment test, the luminescence detection of the present invention measures the light emitted from four test sample wells, called hot wells, of a test plate. In a preferred embodiment, the hot wells are located near each corner of the sample tray used for the alignment testing. The adjacent well crosstalk from each of the four hot wells is analyzed, and the values are compared. When the collimator is aligned precisely over the sample well tray, the crosstalk values will be symmetrical for the four hot wells. The software of the present invention flags any errors detected, such as incorrect number of test sample wells, incorrect intensity, or incorrect location. After the detection of no errors or after the correction of detected and flagged errors, the software of the present invention performs a symmetry calculation to determine precise alignment of the sample well tray, collimator, Fresnel lens and CCD camera assembly. In a known embodiment of the invention, known software techniques are employed to perform the symmetry calculation process by performing the following steps:

1. Extract the hot well and vertical and horizontal adjacent well intensities;
2. Calculate the averages of the horizontal and vertical adjacent well intensities separately for each hot well;
3. Calculate the differences between the actual adjacent intensity vs. the average for each of the horizontal and vertical directions;
4. Normalize the differences by the hot well intensity to convert to a percentage intensity value;
5. Find the worst case absolute value of the differences and display that as the overall misalignment;
6. Calculate the average X-direction (horizontal) misalignment by averaging the four adjacent wells to the right (horizontal direction) of the hot wells;
7. Calculate the average Y-direction (vertical) misalignment by averaging the four adjacent wells to the top (vertical direction) of the hot wells;
8. Calculate the rotational misalignment by averaging the left side hot well vertical adjacent wells at the top of the hot wells, and subtracting that from the average of the right side hot well vertical adjacent wells, thereby indicating any tilt in adjacent well values.

In step A, three actual images for each filter/emitter are taken. $A_1$ is a precursor image, $A_2$ is the full integration time image, and $A_3$ is post-cursor image. The precursor and post-cursor images are taken to avoid the problem of pixel saturation and to extend the detection dynamic range. The precursor and post-cursor images refer to reduced integration time images, which should not contain multiple saturated pixels. If more than six pixels of the full integration time image are saturated, the pre- and post-cursor images are averaged together to form the actual data for that well area. In the absence of six pixel saturation, the full integration time image is used.

In order to clearly isolate and read each pixel, in step B, each image is subjected to edge detection and masking, a processing step whereby the edge of each well or corresponding light image is identified, or annotated, to set off and clearly separate each well region of interest, as disclosed in U.S. patent application Ser. No. 09/351,660, incorporated herein by reference. Again, edge detection and masking is performed for each of $B_1$, $B_2$ and $B_3$, referring to the precursor, full integration time image and post-cursor images, respectively. The images are then subjected to "outlier" correction, correcting or "shaving" outliers and anomalies. In this process, the pixels within the region of interest are examined to identify "outliers"—those that are in gross disagreement with their neighbors, in terms of light intensity detected, and if the intensity of a given pixel or small pixel area is significantly different than neighboring pixels or pixel areas, then the average of the surrounding pixels or areas is used to replace erroneous data. This can be due to random radiation, such as that caused by cosmic rays. In this process, this type of intensity is corrected.

Subsequently, in step C, each image $C_1$, $C_2$ and $C_3$ is subjected to dark subtraction, subtracting the dark background, so as to obtain average pixel values within each mask-defined region of interest. The subtraction is done on a well-by-well basis from stored libraries which are updated periodically.

Specifically, the dark subtraction is conducted to correct for the fact that even in the absence of light, CCD cameras can output low level pixel or bin values. This value includes the electronic bias voltage, which is invariant of position and integration time, and the "dark current," which may vary by position, and is proportional to integration time and to the temperature of the CCD. The CCD may also have faulty pixels that are always high level or saturated regardless of light input.

The processing software of the invention subtracts this background image or data from the real sample well image data in step C. As persons of ordinary skill in the relevant art will recognize, it is known to take a "dark" image immediately before or after a real image, imaging for the same integration time in both cases, and subtracting the "dark" image data from the real image data. In the preferred embodiment of the invention, "dark" image data is collected intermittently, preferably at specific time intervals. The initial "dark" image background data is collected at startup, and then typically at four hour intervals during image processing operations.

Because the background image has an integration time-invariant component and an integration time-variant component, data is collected for each sample well at minimum integration time and at maximum integration time, and a "slope/intercept" line is calculated between the two data points, using known data analysis techniques. This calculation permits data interpolation for any integration time between the minimum and maximum, and also permits data extrapolation for integration times below or beyond the minimum and maximum integration times.

In a preferred embodiment of the invention, a CCD camera is employed that has two separate "dark" current functions, caused by the CCD output amplifier. Operation of the amplifier generates heat and necessarily creates background "dark" image data. In the preferred embodiment, for integration times of less than 10 seconds, the amplifier operates continuously, whereas for integration times of more than 10 seconds, the amplifier remains off until immediately prior to the read operation. The "slope/intercept" line calculated for integration times of more than 10 seconds will then necessarily have a lower slope than a "slope/intercept" line calculated for integration times of less than 10 seconds. In step C, the processing software element allows separate collection and least squares regression for both the 0 to 10 second integration time region a processor 50, the "dark" background image data is stored separately for each individual AOI.

"Dark" current and bias can also vary over time. The processing software element corrects for this effect by comparing the integration time normalized (using the regression line technique described above) "dark reference" pixel values (outside the imaging field-described above), that were taken when the "dark" background images were taken, versus the "dark reference" pixel values taken while real sample well images are being taken. The difference between the values is then subtracted or added, as applicable, as a global number, to the "dark" background data. This corrects for bias drift and also for global CCD temperature drift.

As mentioned, all of the above "dark background" interpolation/subtraction of step C is done on a well by well basis.

At step D, if pixel saturation has occurred such that the average of the pre-cursor and post-cursor image must be used, the image data is multiplied by the reciprocal of the percentage represented by the pre-cursor images (e.g., 3%).

In step E, the well data is corrected for uniformity variations using a calibration file that is the reciprocal of the system response to a perfectly uniform input illumination.

In step F, the cross-talk correction is effected by processing the data as a whole and preparing a final image in much the same fashion as reconstruction of three dimensional images from a two dimensional data array is practiced.

Specifically in a preferred embodiment of step F, the impulse response function (IRF) is collected for all 96 wells of the 96 well plate type. This is done by filling one particular well in a given plate with a high intensity luminescent source, imaging the plate, and analyzing all of the wells in the plate for their response to the one high intensity well. The IRF is collected for all of the wells individually by repeating the process for every different well location desired for the complete data set. For 384 plate types, 96 sampling areas are selected, and data for the wells in between the selected sampled areas are interpolated in two dimensions. In the preferred embodiment, the 96 sampling areas comprise every second row and every second column, starting at the outside and working toward the center. Because in the 384 well plates the number of rows and columns is even, the two center rows and the two center columns are interpolated. The reflections in a 384 well plate are also modeled, and used to predict and interpolate reflections for the missing input data. Further in the preferred embodiment, all wells are normalized to the well with the highest intensity.

Subsequently in step F, the two-dimensional array of well IRF values for each welfare "unfolded" into a one-dimensional column array, and the two-dimensional arrays of IRF values for other wells are added as subsequent columns, as shown in Chart 1 following:

CHART 1

| Unfolded Data Into Column 1 | | | |
|---|---|---|---|
| IRF for A1 | IRF for B1 | IRF for C1 | |
| A1 | A1 | A1 | Etc |
| B1 | B1 | B1 | |
| C1 | C1 | C1 | |
| D1 | D1 | D1 | |
| E1 | E1 | E1 | |
| F1 | F1 | F1 | |
| G1 | G1 | G1 | |
| H1 | H1 | H1 | |
| A2 | A2 | A2 | |
| B2 | B2 | B2 | |
| C2 | C2 | C2 | |
| Etc | Etc | Etc | |

The unfolded matrix, which has the form of an N×N matrix, where N=the number of wells to be corrected, comprises a full characterization of the instrument crosstalk, including reflection factors. This unfolded matrix is then inverted, using known matrix inversion techniques, and used as a correction to matrix multiply a one-dimensional matrix unfolded from real assay data. This arithmetic process may be shown as matrix algebra:

[true source distribution]×[system IRF]=[instrument output] solving for [true source distribution] produces

[true source distribution]={1/[system IRF]}×[instrument output]

Subsequently, the calculated well intensities resulting from the above processing are calibrated to an absolute parameter of interest, such as the concentration of a known reporter enzyme. This calibration is conducted through a normalization process producing any of a variety of calibration curves, which will be familiar to those of ordinary skill in the relevant art.

In optional step G, the processed image information is subjected to any necessary post adjustment processing, for appropriate correlation with the materials tested. Specifically, in a preferred embodiment, the processing software of the present invention is capable of performing multi-component analysis. The basic problem is to calculate separately the concentration of a single reagent in a single sample containing other different reagents. Typically, the reagents used with the invention are formulated so as to emit over different, but perhaps overlapping, spectrums. As earlier described with respect to the integrated optical element, the first step of separating the light from multiple reagents is accomplished by optical bandpass filters, which are designed to maximize the sensitivity of the target reagent emission, while minimizing the sensitivity to other non-target reagent emission. In the present embodiment of the invention, there is one optical filter for each target reagent emission spectrum.

Since optical filters are interference devices, their bandpass characteristics vary, dependent on the angle of incidence of the emission to be filtered. The angle of incidence will be unique for each well because each well's specific location is unique relative to the optical filter. Accordingly, all calculations and filter coefficients must be unique per sample well. The multi-component calibration is performed as follows:

Prior to the real multiplexed (multiple reagent) samples, standards containing only a single reagent in each well are imaged and analyzed. These standards will produce a set of coefficients to be used collectively as multi-component coefficients for each optical filter, for each well. For a given optical filter, the target reagent for that filter should produce the highest output. The other reagents may also have spectra in the filter's bandpass, and will produce smaller outputs, which are a measure of the overlap of those nontarget reagent spectra into the filter signal. For example, the filter's output for the target reagent might be 850, and the filter's output for the other 2 reagents might be 100 and 50, respectively. If the 3 reagents were added together in a single well, the total output would be 1000, and the proportions would be 850:100:50. These coefficients are measured for each well location and filter separately, which gives a complete set of coefficients for simultaneous equations. This will allow a solution for any combination of concentrations of reagent in one sample well. Further in the preferred embodiment, these coefficients will also be normalized by the total intensity read in the "total emission" filter, so that the calculation will result in the same intensity as the instrument would measure if only a single reagent was measured by the "total emission" filter. This calculation may be shown as follows for a simple case of blue and green reagents (abbreviated as R in the calculations), and blue and green and total emission filters (abbreviated as F in the calculations):

Let $A$=(output of the instrument for blue $R$ thru the blue $F$)/(output of instrument for blue $R$ thru total emission $F$);

Let $B$=(output of the instrument for green $R$ thru the blue $F$)/(output of instrument for green $R$ thru total emission $F$);

Let $C$=(output of the instrument for blue $R$ thru the green $F$)/(output of instrument for blue $R$ thru total emission $F$);

Let $D$=(output of the instrument for green $R$ thru the green $F$)/(output of instrument for green $R$ thru total emission $F$);

These coefficients are measured for each well prior to running a multi-color run.
Then for a multi-reagent/color run, (output of the instrument for the blue $F$)=$A$×(true intensity of blue $R$)+$B$×(intensity of green $R$); and (output of the instrument for the green $F$)=$C$×(true intensity of blue $R$)+$D$×(intensity of green $R$)

These 2 simultaneous equations are then solved for the true intensity of the blue and green reagents by the processing software, under control of processor 50.

Further in step G, the raw output of the instrument for each filter is normalized for integration time before solving the equations.

The resulting intensities could then be calibrated as concentration by use of standards as described in the previous section.

Finally, in step H, the analyzed data is presented in a user-acceptable format, again controlled by processor 50.

The invention may be further understood by reference to examples of assays practiced in HTS format, demonstrating the dynamic range and flexibility of the NorthStar™ luminometer.

EXAMPLES

Example 1

Figure 8:
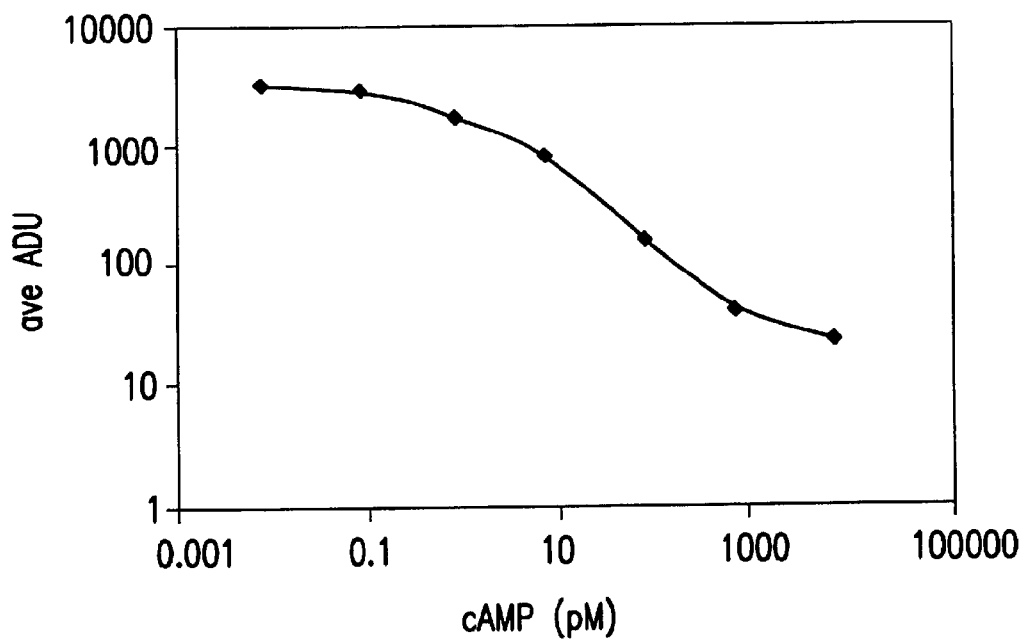
FIGS. 8-15 are illustrations of the results obtained using the invention in Examples 1-10, respectively.

Purified cAMP Quantitation cAMP standards were serial diluted and added to a 96-well assay plate with alkaline phosphatase conjugated cAMP and anti-cAMP. Plates were processed with the cAMP-Screen™ protocol and imaged for 1 minute on the NorthStar™ 30 minutes after addition of CSPD®/Sapphire-II™. A sensitivity of 0.06 pM of purified cAMP is achieved with cAMP-Screen™ on the NorthStar™ workstation. The results are depicted in FIG. 8.

Example 2 cAMP Induction in Adrenergic β2 Receptor-Expressing C2 Cells

Figure 9:
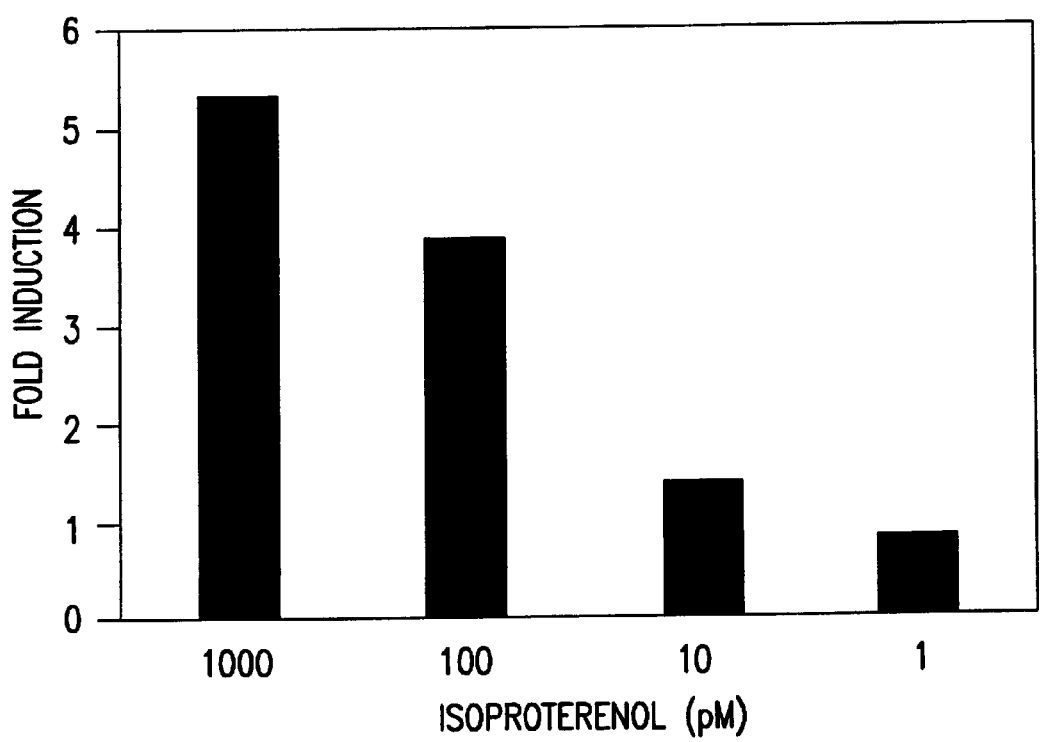

Adrenergic β2 Receptor-expressing C2 cells were plated in a 96-well plate (10,000 cells/well) and stimulated with isoproterenol for 10 minutes. cAMP production was quantitated in cell lysates using the cAMP-Screen™ assay. The assay plate was imaged for 1 minute on the NorthStar™, 30 minutes after addition of CSPD®/Sapphire-II™. Increasing cAMP levels were detected on the NorthStar™ from the stimulated adrenergic receptor. The results are depicted in FIG. 9.

Example 3

Figure 10:
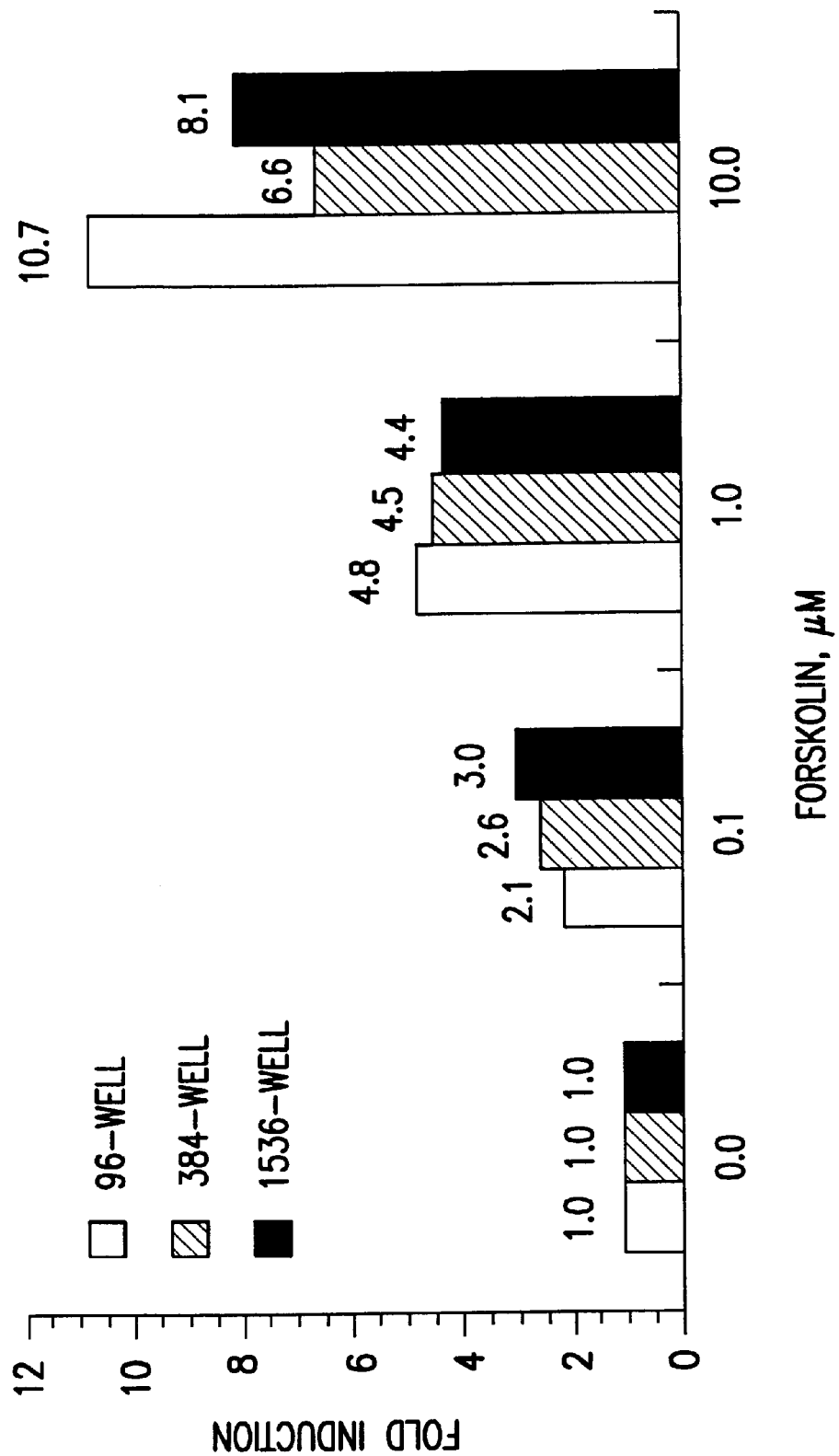

Luc-Screen™ Reporter Gene Assay in 96-, 384- and 1,536-well Format pCRE-Luc-Transfected cells were seeded in 96-, 384- and 1,536-well plates, incubated for 20 hours with forskolin, and assayed with the Luc-Screen™ system. PCRE-Luc contains the luciferase reporter gene under the control of a cAMP response element (CRE). Forskolin induces intracellular cAMP production through the irreversible activation of adenylate cyclase. All plate formats demonstrate comparable forskolin-induced cAMP levels. The results are depicted in FIG. 10.

Example 4

Figure 11:
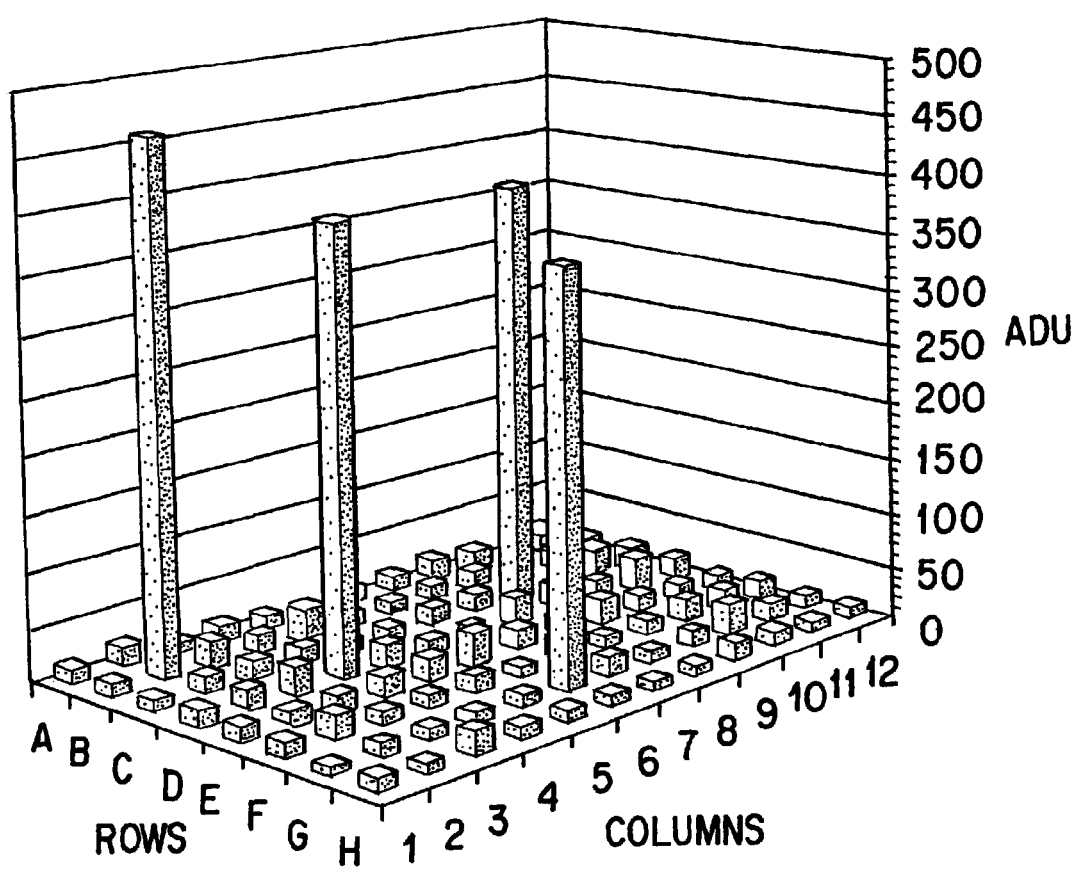

Forskolin Induction of pCRE-Luc Transfected NIH-3T3 Cells pCRE-Luc-Transfected cells were seeded in a 96-well plate. Four random wells were induced for 17 hours with 1 mM forskolin and the entire plate was assayed with the Luc-Screen™ system. The results are shown in FIG. 11.

Example 5

Dual-Light® Quantitation of Luciferase & β-Galactosidase Reporter Enzymes

Figure 12:
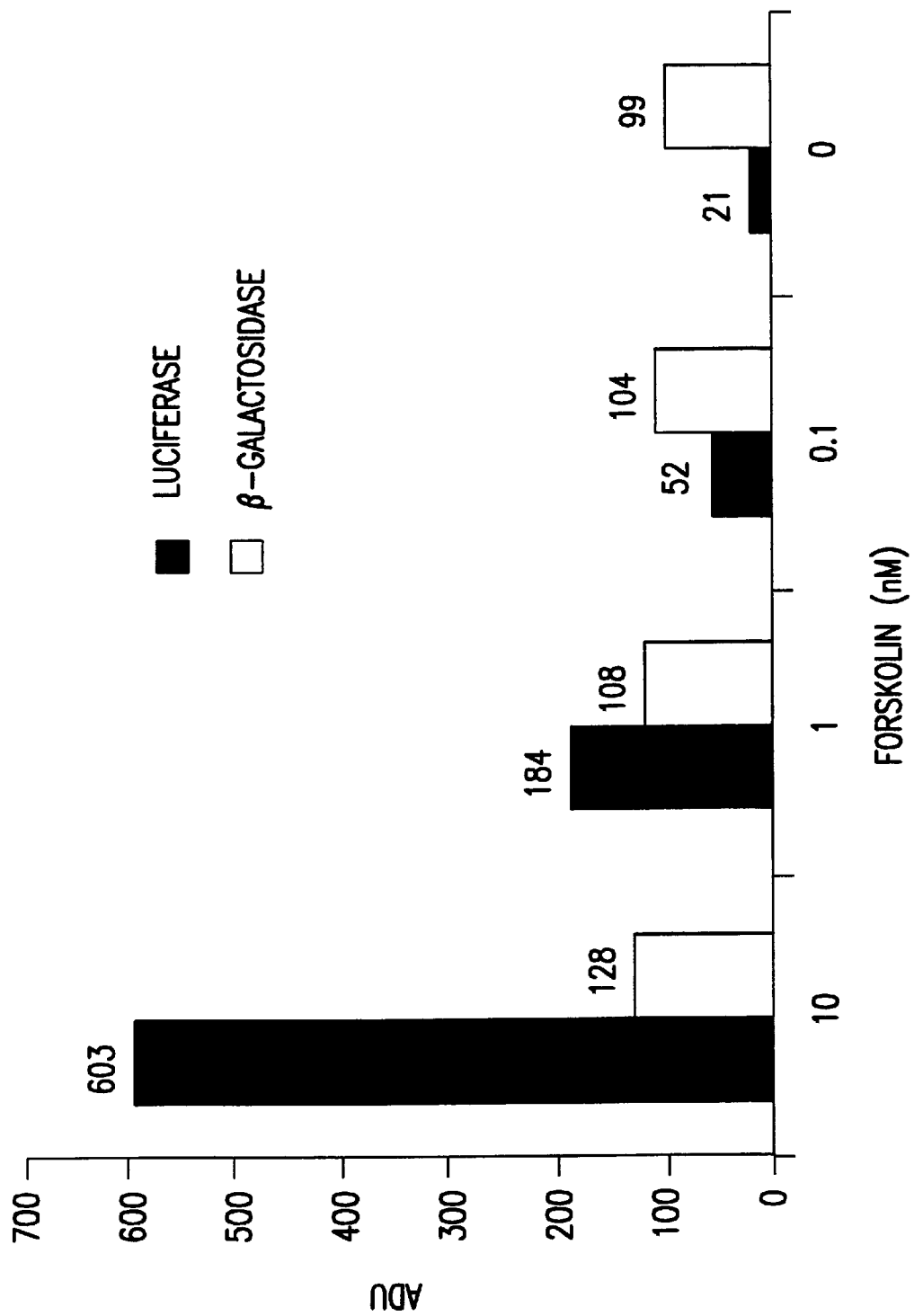

NIH/3T3 cells were co-transfected with pCRE-Luc and pβgal-Control, and seeded into a 96-well microplate ($2\times10^4$ cells/well). Cells were incubated with forskolin for 17 hours. Modified Dual-Light® Buffer A was added to cells and incubated for 10 minutes. Modified Dual Light® Buffer B was injected and luciferase-catalyzed light emission was measured immediately. Thirty minutes later, Accelerator-II was added, and then β-galactosidase-catalyzed light emission was quantitated on the NorthStar™ HTS workstation. Quantitation is shown graphically in FIG. 12.

Example 6

Normalized Fold Induction of Luciferase Reporter

Figure 13:
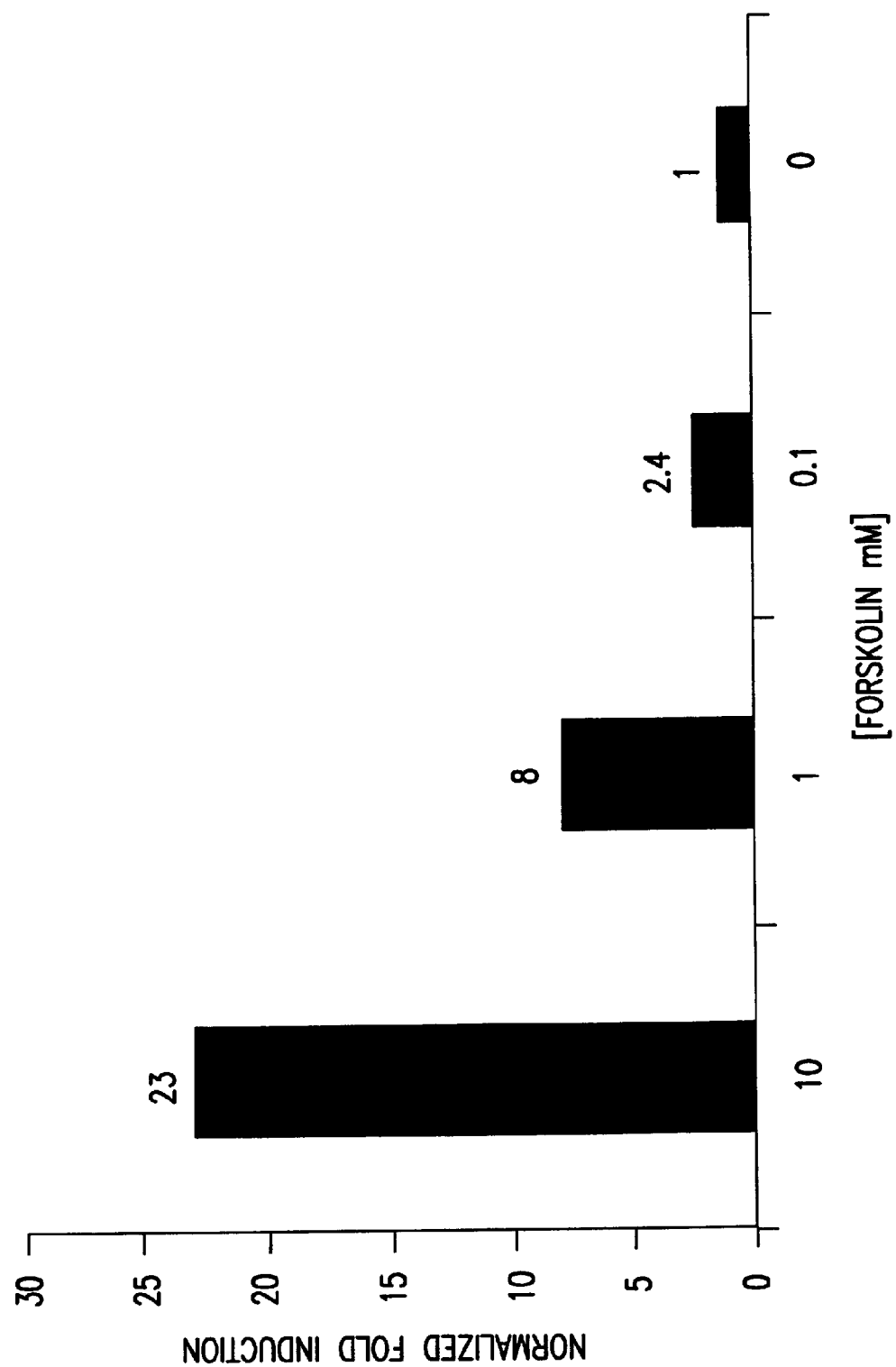

Fold induction of luciferase activity was calculated following normalization to β-galactosidase activity. The Dual-Light® assay enables the use of a control reporter for normalization, or to monitor non-specific effects on gene expression. This is depicted in FIG. 13.

Example 7

Effect of BAPTA-AM on Antagonist Activity

Figure 14:
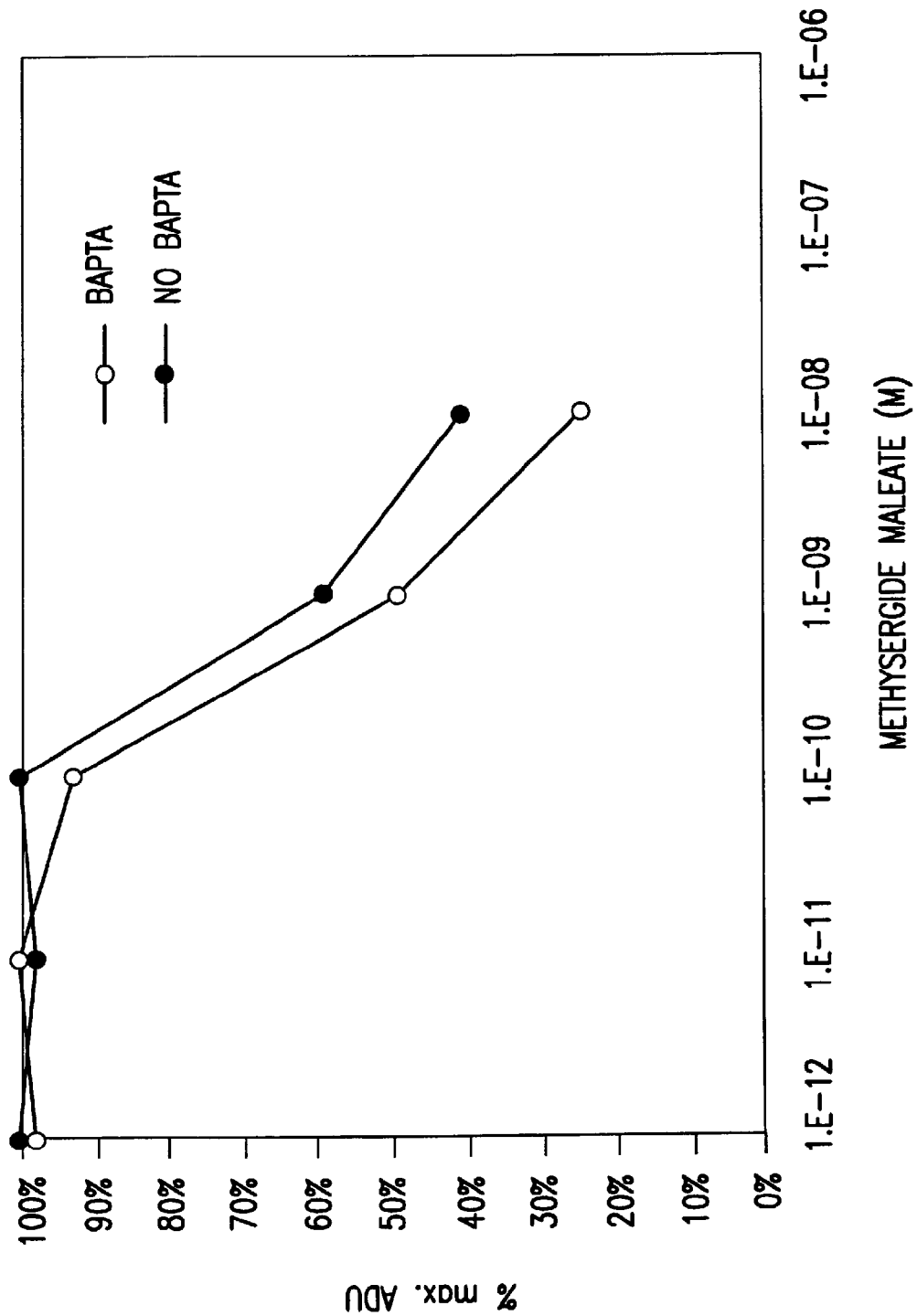

CHO-Aeq-5HT2B cells were loaded with coelenterazine h+/−0.5 µM BAPTA-AM for 4 hours. The antagonist methysergide was added to the charged cells for 30 minutes. 1 µM agonist a-Me-5HT was injected, and the emitted light was integrated for 20 seconds on the NorthStar™ system. The reported 1050 for methysergide (0.6 nM) is unchanged in the presence of BAPTA-AM. The data obtained appears in FIG. 14.

Example 8

Effect of BAPTA-AM on Peptide Agonist Stimulated of the Orexin 2 Receptor

Figure 15:
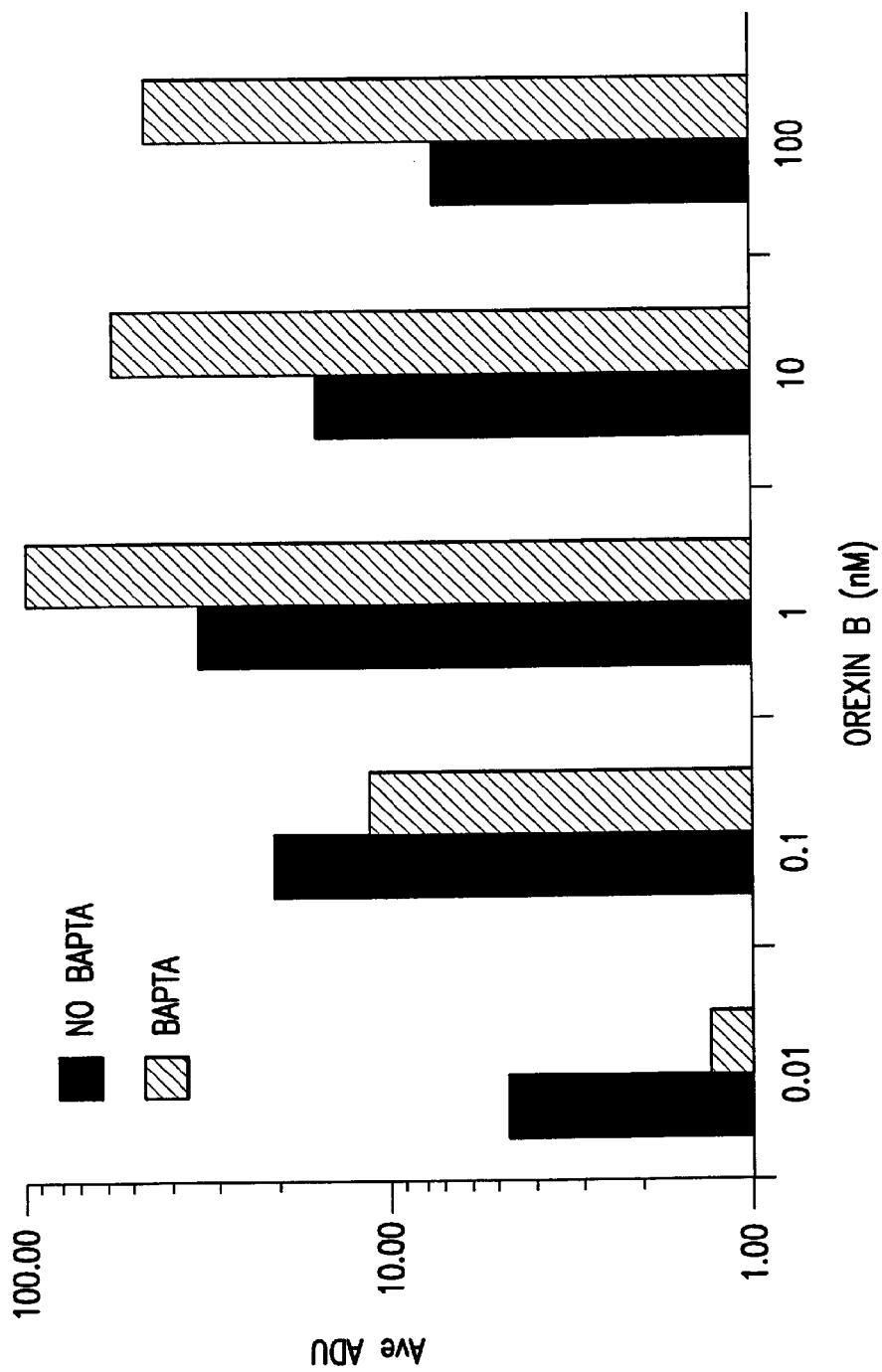

CHO-Aeq-OX2-A2 cells (Euroscreen) were loaded with coelenterazine h+/−0.6 µM BAPTA-AM for 4 hours. The peptide agonist Orexin B was injected into the wells, and the emitted light was integrated for 20 seconds on the NorthStar™. Using this assay on the NorthStar™ system, the reported EC50 for Orexin B (0.75 nM) is unchanged in the presence of BAPTA-AM. This is shown in FIG. 15.

This invention has been described generically, by reference to specific embodiments and by example. Unless so indicated, no embodiment or example is intended to be limiting. Alternatives will occur to those of ordinary skill in the art without the exercise of inventive skill, and within the scope of the claims set forth below.

What is claimed is:

1. A luminescence detecting apparatus, comprising:
   a photosensitive detector;
   a sample chamber configured for placement of a plurality of wells containing respective luminescent samples;
   a substrate comprising a two-dimensional array of openings and positioned during use between the plurality of wells and the detector, the plurality of wells aligned during use to respective ones of the corresponding array of openings, the array of openings configured to simultaneously pass emissions from at least some of the wells to the photosensitive detector and to block some of the emissions from being received by the photosensitive detector;

a lens disposed along an optical path between the two-dimensional array of openings and the detector; and wherein the two-dimensional array of openings is disposed along an optical axis thereof, the only light from the sample wells received by the detector during use is light from the sample wells that is parallel or semi-parallel to the optical axis.

2. The apparatus of claim 1, wherein the apparatus comprises a luminometer.

3. The apparatus of claim 1, further comprising a central processing unit for controlling the analysis of the plurality of luminescent samples.

4. The apparatus of claim 1, further comprising a defogger configured to prevent condensation.

5. The apparatus of claim 1, further comprising a heater disposed below the plurality of wells during use.

6. The apparatus of claim 1, further comprising a plurality of wells, wherein the detector is configured to sequentially detect light at different wavelengths emitted from the plurality of wells.

7. The apparatus of claim 1, further comprising a plurality of luminescent samples disposed within respective ones of the plurality of wells during use.

8. The apparatus of claim 7, wherein each of the plurality of luminescent samples is one of a bioluminescent material or a chemiluminescent material.

9. The apparatus of claim 1, further comprising a plurality of wells, wherein the wells are disposed on a plate.

10. The apparatus of claim 1, further comprising a filter disposed along the optical path between the two-dimensional array of openings and the detector, the filter configured to permit passage of a specific wavelength of light emitted from the wells.

11. The apparatus of claim 1, wherein the two-dimensional array of openings is in close proximity to the plurality of wells during use, so as to enhance restriction of stray light from the wells.

12. The apparatus of claim 1, wherein the lens comprises at least one of a Fresnel lens, an aspheric lens, or a molded plastic lens.

13. The apparatus of claim 1, wherein:
the detector comprises a charge coupled device (CCD);
the lens is a primary lens and the apparatus further comprises a camera lens disposed between the primary lens and the CCD; and
the camera lens is configured to simultaneously image the luminescent samples of more than one of wells.

14. The apparatus of claim 1, further comprising a temperature controller, wherein the sample chamber is temperature controlled for elevating the sample chamber above an ambient temperature.

15. The apparatus of claim 1, wherein the plurality of wells are in simultaneous optical communication with the photosensitive detector, and wherein the photosensitive detector and the two-dimensional array of openings together are configured to simultaneously detect the plurality of respective luminescent samples contained in the plurality of wells.

16. The apparatus of claim 14, wherein the sample chamber comprises a bottom surface and the substrate is positioned during use above the sample chamber.

17. A method for analyzing a plurality of luminescent samples, comprising the steps of:
placing a plurality of luminescent samples in a respective plurality of sample wells;
placing the plurality of sample wells in a luminescence detecting apparatus, the luminescence detecting apparatus comprising a plurality of photosensitive detector elements, a first lens, and a substrate comprising a two-dimensional array of openings;
registering the plurality of sample wells to respective openings of the two-dimensional array of openings;
passing emissions from at least some of the wells through the two-dimensional array of openings to respective ones of the plurality of photosensitive detector elements;
using the substrate to prevent some of the emissions from the at least some of the wells from being received by the photosensitive detector elements;
wherein the two-dimensional array of openings is disposed along a plurality of optical paths between at least two of the sample wells and respective photosensitive detector elements of the plurality of photosensitive detector elements;
wherein the first lens is disposed along at least one of the optical paths at a location between the substrate and the detector; and
wherein the substrate is configured such that the only light from the sample wells received by the detector is light that is parallel or semi-parallel to an optical axis of first lens.

18. The method of claim 17, further comprising positioning a second lens disposed along the optical path at a location between the first lens and the detector.

19. The method of claim 17, wherein the sample chamber comprises a bottom surface and the substrate is positioned during use above the sample chamber.

20. A luminescence detecting apparatus, comprising:
a detector comprising a plurality of photosensitive elements;
a sample chamber configured for placement of a plurality of wells containing respective luminescent samples;
a substrate comprising a two-dimensional array of openings positioned during use between the plurality of wells and the photosensitive elements, the array of openings configured to simultaneously pass emissions from at least some of the wells to respective photosensitive elements of the detector and to block some of the emissions from being received by the respective photosensitive elements;
a lens disposed along an optical path between an opening of the substrate and a respective photosensitive element of the detector; and
a heater disposed during use below the sample chamber.

21. The apparatus of claim 20, further comprising a defogger configured to prevent condensation.

22. The apparatus of claim 20, further comprising a plurality of sample wells disposed within the sample chamber and aligned to corresponding openings of the array of openings.

23. The apparatus of claim 20, wherein the two-dimensional array of openings is disposed along an optical axis thereof, the only light from the sample wells received by the detector is light from the sample wells that is parallel or semi-parallel to the optical axis.

24. The apparatus of claim 20, wherein the detector is configured to sequentially detect light at different wavelengths emitted from the plurality of sample wells.

25. The apparatus of claim 20, wherein each of the plurality of luminescent samples is one of a bioluminescent material or a chemiluminescent material.

26. The apparatus of claim 20, further comprising a filter disposed along the optical path between the two-dimensional array of openings and the detector, the filter configured to permit passage of a specific wavelength of light emitted from the sample wells.

27. The apparatus of claim 20, wherein the two-dimensional array of openings is in close proximity to the plurality of sample wells so as to enhance restriction of stray light from the sample wells.

28. The apparatus of claim 20, wherein:

the detector comprises a charge coupled device (CCD);

the at least one lens comprises a primary lens and secondary lens disposed between the primary lens and the CCD; and the secondary lens is configured to simultaneously image the luminescent samples of more than one of wells.

29. The apparatus of claim 20, further comprising a temperature controller, wherein the sample chamber is temperature controlled for elevating the sample chamber above an ambient temperature.

30. The apparatus of claim 20, wherein the plurality of wells are in simultaneous optical communication with the photosensitive detector, and wherein the photosensitive detector and the two-dimensional array of openings together are configured to simultaneously detect the plurality of respective luminescent samples contained in the plurality of wells.

31. The apparatus of claim 20, further comprising a plurality of wells containing respective luminescent samples, wherein the array of openings simultaneously pass emissions from at least some of the wells to respective photosensitive elements of the detector and block some of the emissions from being received by the respective photosensitive elements.

32. The apparatus of claim 20, wherein the sample chamber comprises a bottom surface and the substrate is positioned during use above the sample chamber.

* * * * *